US008715932B2

(12) United States Patent
Su et al.

(10) Patent No.: US 8,715,932 B2
(45) Date of Patent: May 6, 2014

(54) NUCLEIC ACID SEQUENCING

(75) Inventors: Xing Su, Cupertino, CA (US); Kai Wu, Mountain View, CA (US); Liming Wang, Santa Clara, CA (US); Jianquan Liu, Fremont, CA (US); Grace M. Credo, San Mateo, CA (US)

(73) Assignee: Intel Corporation, Santa Clara, CA (US)

( * ) Notice: Subject to any disclaimer, the term of this patent is extended or adjusted under 35 U.S.C. 154(b) by 348 days.

(21) Appl. No.: 12/860,462

(22) Filed: Aug. 20, 2010

(65) Prior Publication Data

US 2012/0046176 A1  Feb. 23, 2012

(51) Int. Cl.
*C12Q 1/68* (2006.01)
(52) U.S. Cl.
USPC ........................................................ 435/6.11
(58) Field of Classification Search
None
See application file for complete search history.

(56) References Cited

U.S. PATENT DOCUMENTS

| | | | |
|---|---|---|---|
| 5,795,714 | A | 8/1998 | Cantor et al. |
| 5,849,487 | A | 12/1998 | Hase et al. |
| 6,232,075 | B1 | 5/2001 | Williams |
| 6,613,523 | B2 | 9/2003 | Fischer |
| 6,952,651 | B2 | 10/2005 | Su |
| 6,972,173 | B2 | 12/2005 | Su et al. |
| 7,005,264 | B2 | 2/2006 | Su et al. |
| 7,211,390 | B2 | 5/2007 | Rothberg et al. |
| 7,238,477 | B2 | 7/2007 | Su et al. |
| 7,476,501 | B2 | 1/2009 | Chan et al. |
| 7,488,578 | B2 | 2/2009 | Gumbrecht et al. |
| 7,575,865 | B2 | 8/2009 | Leamon et al. |
| 8,262,900 | B2 | 9/2012 | Rothberg et al. |
| 8,524,057 | B2 | 9/2013 | Rothberg et al. |
| 2002/0187515 | A1 | 12/2002 | Chee et al. |
| 2003/0116723 | A1 | 6/2003 | Yoshida |
| 2003/0152985 | A1 | 8/2003 | Pourmand et al. |
| 2003/0215816 | A1 | 11/2003 | Sundararajan et al. |
| 2003/0215862 | A1 | 11/2003 | Parce et al. |
| 2004/0110208 | A1 | 6/2004 | Chan et al. |
| 2004/0197793 | A1 | 10/2004 | Hassibi et al. |
| 2004/0229247 | A1 | 11/2004 | DeBoer et al. |
| 2004/0259105 | A1 | 12/2004 | Fan et al. |
| 2005/0019784 | A1 | 1/2005 | Su et al. |
| 2005/0026163 | A1 | 2/2005 | Sundararajan et al. |
| 2005/0106587 | A1 | 5/2005 | Klapproth et al. |
| 2005/0186576 | A1 | 8/2005 | Chan et al. |
| 2005/0214759 | A1 | 9/2005 | Wlassof et al. |
| 2006/0029969 | A1 | 2/2006 | Su et al. |
| 2006/0068440 | A1 | 3/2006 | Chan et al. |
| 2006/0105373 | A1 | 5/2006 | Pourmand et al. |
| 2006/0199193 | A1 | 9/2006 | Koo et al. |
| 2007/0231795 | A1 | 10/2007 | Su |
| 2008/0032297 | A1 | 2/2008 | Su et al. |
| 2009/0170716 | A1 | 7/2009 | Su et al. |
| 2010/0167938 | A1 | 7/2010 | Su et al. |
| 2010/0267013 | A1 | 10/2010 | Su et al. |

FOREIGN PATENT DOCUMENTS

WO         2003/054225 A2        7/2003

OTHER PUBLICATIONS

Nallur et al (Nucleic Acids Res. 29: e118 (2001)).*
Koo et al., U.S. Appl. No. 11/073,160, entitled "Sensor Arrays and Nucleic Acid Sequencing Applications", filed Mar. 4, 2005, 31 pages.
Su et al., U.S. Appl. No. 12/459,309, entitled "Chemically Induced Optical Signals and DNA Sequencing", filed Jun. 30, 2009, 45 pages.
Liu et al., U.S. Appl. No. 12/655,459, entitled "Solid-Phase Chelators and Electronic Biosensors", filed Dec. 30, 2009, 58 pages.
Elibol et al., U.S. Appl. No. 12/655,578, entitled "Nanogap Chemical and Biochemical Sensors", filed Dec. 31, 2009, 49 pages.
Liu et al., U.S. Appl. No. 12/823,995, entitled "Nucleotides and Oligonucleotides for Nucleic Acid Sequencing", filed Jun. 25, 2010, 50 pages.
Peng et al., "Polymerase-Directed Synthesis of 2'-Deoxy-2'-fluoro-β-D-arabinonucleic Acids," Journal of American Chemical Society, vol. 129, No. 17, Apr. 10, 2007, pp. 5310-5311.
Watts et al., "2'F-Arabinonucleic acids (2'F-ANA)—History, properties, and new frontiers," Canadian Journal of Chemistry, vol. 86, No. 7, Jul. 1, 2008 , pp. 641-656.
Bentley et al., "Accurate whole human genome sequencing using reversible terminator chemistry," Nature, vol. 456, Nov. 6, 2008, pp. 53-59.
Dahl et al., "Circle-to-circle amplification for precise and sensitive DNA analysis," Proceedings of the National Academy of Sciences (PNAS), vol. 101, No. 13, Mar. 30, 2004, pp. 4548-4553.
Niclass et al., "A Single Photon Avalanche Diode Implemented in 130-nm CMOS Technology," IEEE Journal of Selected Topics in Quantum Electronics, vol. 13, No. 4, Jul./Aug. 2007, pp. 863-869.
Elibol et al., "Nanoscale thickness double-gated field effect silicon sensors for sensitive pH detection in fluid," Applied Physics Letters, vol. 92, No. 19, May 2008, pp. 193904-1 to 193904-3.
Gabig-Ciminska et al., "Electric chips for rapid detection and quantification of nucleic acids," Biosensors and Bioelectronics, vol. 19, 2004, pp. 537-546.
Guo et al., "Four-color DNA sequencing with 3'-O-modified nucleotide reversible terminators and chemically cleavable fluorescent dideoxynucleotides," Proceedings of the National Academy of Sciences (PNAS), vol. 105, No. 27, Jul. 8, 2008, pp. 9145-9150.
Kling, "Ultrafast DNA sequencing," Nature Biotechnology, Nature Publishing Group, vol. 21, No. 12, Dec. 2003, pp. 1425-1427.

(Continued)

*Primary Examiner* — James Martinell

(57) ABSTRACT

Nucleic acid sequencing using concatemers of DNA is provided. Optionally, amplified reaction products from the repeated incorporation and excision of a nucleoside complementary to a nucleoside of the DNA to be sequenced onto primer molecules hybridized to the concatemers of DNA are detected. Nucleic acid sequencing using concatemers of DNA and non-natural oligonucleotides is also provided. Nucleic acid sequencing reactions are detected electronically and or optically using arrays of detectors.

21 Claims, 10 Drawing Sheets

(56) References Cited

OTHER PUBLICATIONS

Ronaghi et al., "DNA Sequencing: A Sequencing Method Based on Real-Time Pyrophosphate," Science Magazine, vol. 281, No. 5375, Jul. 17, 1998, pp. 363-365.

Seeberger et al., "2'-Deoxynucleoside Dithiophosphates: Synthesis and Biological Studies," Journal of American Chemical Society, vol. 117, No. 5, Feb. 1995, pp. 1472-1478.

Yeung et al., "Electrochemical Real-Time Polymerase Chain Reaction," Journal of American Chemical Society, vol. 128, No. 41, Sep. 23, 2006, 4 pages.

Kruppa et al., "Reversible Coordinative Bonds in Molecular Recognition," Chemical Reviews, vol. 106, No. 9, Aug. 10, 2006, pp. 3520-3560.

Levene et al., "Zero-Mode Waveguides for Single-Molecule Analysis at High Concentrations," Science Magazine, Reports, vol. 299, No. 5607, Jan. 31, 2003, pp. 682-686.

Zhou et al., "Quantitative detection of single nucleotide polymorphisms for a pooled sample by a bioluminometric assay coupled with modified primer extension reactions (BAMPER)," Nucleic Acids Research, vol. 29, No. 19: e93, 2001, pp. 1-11.

Gao, Guangxia, et al., "Conferring RNA polymerase Activity to a DNA polymerase: A single residue in reverse transcriptase controls substrate selection," Proc. Natl. Acad. Sci. USA, 1997, pp. 407-411, vol. 94.

Delucia, Angela M., et al., "An error-prone family Y DNA polymerase (Din B homolog from Sulfolobus solfataricus) uses a 'stericgate' residue for discrimination against ribonucleotides," Nucleic Acids Research, 2003, pp. 4129-4137, vol. 31. No. 14.

Czarnik, Anthony W., "Chemical Communication in Water Using Fluorescent Chemosensors," Acc. Chem. Res., 1994, pp. 302-308, vol. 27.

Rosenblum, B.B., et al., "New Dye-Labeled Terminators for Improved DNA Sequencing Patterns," Nucleic Acids Research, 1997, pp. 4500-4504, vol. 25, No. 22.

Ju, Jingyue, et al., "Fluorescence Energy Transfer Dye-Labeled Primers for DNA Sequencing and Analysis," Proc. Natl. Acad. Sci, USA, Biophysics, 1995, pp. 4347-4351, vol. 92.

Lieberwirth, Ulrike, et al., "Multiplex Dye DNA Sequencing in Capillary Gel Electrophoresis by Diode Laser-Based Time-Resolved Fluorescence Detection," Analytical Chemistry, 1998, pp. 4771-4779, vol. 70, No. 22.

Kim, Sook Kyung, et al., "Chemosensors for Pyrophosphate," Accounts of Chemical Research, 2008, pp. 23-31, vol. 42, No. 1.

Lee, Thomas Ming-Hung, et al., "Microfabricated PCR-electrochemical device for simultaneous DNA amplification and detection," Lab on a Chip, Apr. 17, 2003, pp. 100-105, vol. 3.

"Description of Therminator Polymerase", Retrieved on Sep. 13, 2013, Webpage available at: https://www.neb.com/products/m0266-therminator-ii-dna-polymerase.

Gardner, A.F. et al. "Acyclic and dideoxy terminator preferences denote divergent sugar recognition by archaeon and Taq DNA polymerases," Nucleic Acids Research, 2002, pp. 605-613, vol. 30, No. 2.

Ju, J. et al., "Four-color DNA Sequencing by Synthesis Using Cleavable Fluorescent Nucleotide Reversible Terminators," Proc. Natl. Acad. Sci., 2006, pp. 19635-19640, vol. 103, No. 52.

Yang, Z. et al., "Nucleoside Alpha-thiotriphosphates, Polymerases and the Exonuclease III Analaysis of Oligonucleotides Containing Phosphorothioate Linkages," Nucleic Acids Research, 2007, pp. 3118-3127, vol. 35, No. 9.

Fuller, C.W. et al., "The Challenges of Sequencing by Synthesis," Nature Biotechnology, 2009, pp. 1013-1023, vol. 27, No. 11.

Eid, J. et al., "Real-Time DNA Sequencing from Single Polymerase Molecules," Science, 2009, pp. 133-138, vol. 323.

Marcel Margulies et al., "Genome sequencing in microfabricated high-density picoliter reactors," Nature, 2005, pp. 376-380, vol. 437.

\* cited by examiner

NUCLEIC ACID SEQUENCING

CROSS REFERENCE TO RELATED APPLICATIONS

The present application is related to U.S. patent application Ser. No. 11/226,696, entitled "Sensor Arrays and Nucleic Acid Sequencing Applications," filed Sep. 13, 2005, now pending, which is a continuation-in-part application that claims the benefit of U.S. patent application Ser. No. 11/073,160, entitled "Sensor Arrays and Nucleic Acid Sequencing Applications," filed Mar. 4, 2005, and is also related to U.S. patent application Ser. No. 11/967,600, entitled "Electronic Sensing for Nucleic Acid Sequencing," filed Dec. 31, 2007, now pending, U.S. patent application Ser. No. 12/319,168, entitled "Nucleic Acid Sequencing and Electronic Detection," filed Dec. 31, 2008, now pending, U.S. patent application Ser. No. 12/459,309, entitled "Chemically Induced Optical Signals," filed Jun. 30, 2009, now pending, U.S. patent application Ser. No. 12/655,459, entitled "Solid-Phase Chelators and Electronic Biosensors," filed Dec. 30, 2009, now pending, U.S. patent application Ser. No. 12/655,578, entitled "Nanogap Chemical and Biochemical Sensors," filed Dec. 31, 2009, now pending, and U.S. patent application Ser. No. 12/823,995, entitled "Nucleotides and Oligonucleotides for Nucleic Acid Sequencing," filed Jun. 25, 2010, now pending, the disclosures of which are incorporated herein by reference.

BACKGROUND OF THE INVENTION

1. Field of the Invention

Embodiments of the present invention relate generally to the detection of nucleic acids, the electronic and optical detection of nucleic acids, nucleic acid sequencing reactions, and nucleic acid sequencing.

2. Background Information

Genetic information in living organisms is contained in very long polymeric molecules known as nucleic acids. Typical nucleic acids are deoxyribonucleic acid (DNA) and ribonucleic acid (RNA). Naturally occurring DNA and RNA molecules are generally composed of four different chemical building blocks called nucleotides which are in turn made up of a sugar (deoxyribose or ribose, respectively), phosphoric acid, and one of five bases, adenine (A), cytosine (C), guanine (G), and thymine (T) or uracil (U). The human genome contains approximately three billion base pairs and an estimated 20,000 to 25,000 genes. A genome is all the genetic material in a cell's chromosomes. DNA sequence information can be used to determine multiple characteristics of an individual as well as the presence of and or susceptibility to many common diseases, such as cancer, cystic fibrosis, and sickle cell anemia. Further, knowledge of an individual's genome provides an opportunity to personalize medical treatments since, for example, certain drugs are (or may be) only or most effective in individuals having a specific genetic makeup. The effectiveness of newly discovered drugs can also be mapped out based on genetics. As a result of genetic information, time wasted in an ineffective treatment and side effects from treatment(s) can be avoided for individuals whose genetic make up indicates that they will not benefit from a treatment. Determination of the entire three billion nucleotide sequence of the human genome has provided a foundation for identifying the genetic basis of diseases. The first determination of the entire sequence of the human genome required years to accomplish. The need for nucleic acid sequence information also exists in research, environmental protection, food safety, biodefense, and clinical applications, such as for example, pathogen detection, i.e., the detection of the presence or absence of pathogens or their genetic variants.

Thus, because DNA sequencing is an important technology for applications in bioscience, such as, for example, the analysis of genetic information content for an organism, tools that allow for faster and or more reliable sequence determination are valuable. Applications such as, for example, population-based biodiversity projects, disease detection, personalized medicine, prediction of effectiveness of drugs, and genotyping using single-nucleotide polymorphisms, stimulate the need for simple and robust methods for sequencing short lengths of nucleic acids (such as, for example, those containing 1-20 bases). Sequencing methods that provide increased accuracy and or robustness, decreased need for analysis sample, and or high throughput are valuable analytical and biomedical tools.

Additionally, molecular detection platforms that are miniaturized and manufacturable in high volumes provide access to affordable disease detection to many people in places and situations in which such access was not in the past possible. The availability of affordable molecular diagnostic devices reduces the cost of and improves the quality of healthcare available to society. Additionally, portable molecular detection devices have applications in security and hazard detection and remediation fields and offer the ability to immediately respond appropriately to a perceived security or accidental biological or chemical hazard.

DETAILED DESCRIPTION OF THE INVENTION

Embodiments of the invention provide methods and devices that are useful for sequencing polymers of nucleic acids. In general, nucleic acids (polynucleotides) that can be sequenced include polymers of deoxyribonucleotides (DNA) or ribonucleotides (RNA) and analogs thereof that are linked together by a phosphodiester bond. A polynucleotide can be a genome, a portion of a genome, a gene or a portion thereof, a cDNA, a synthetic polydeoxyribonucleic acid sequence, or RNA (ribonucleic acid). A polynucleotide, including an oligonucleotide (for example, a probe or a primer) can contain nucleoside or nucleotide analogs, or a backbone bond other than a phosphodiester bond. In general, the nucleotides in a polynucleotide are naturally occurring deoxyribonucleotides (or deoxyribonucleosides), such as adenine, cytosine, guanine or thymine linked to 2'-deoxyribose, or ribonucleotides (or ribonucleosides) such as adenine, cytosine, guanine or uracil linked to ribose. However, a polynucleotide or oligonucleotide also can contain nucleotide analogs, including non-naturally occurring synthetic nucleotides or modified naturally occurring nucleotides.

The covalent bond linking the nucleotides of a polynucleotide generally is a phosphodiester bond. However, the covalent bond also can be any of a number of other types of bonds, including a thiodiester bond, a phosphorothioate bond, a peptide-like amide bond or any other bond known to those in the art as useful for linking nucleotides (nucleosides) to produce synthetic polynucleotides. The incorporation of non-naturally occurring nucleotide analogs or bonds linking the nucleotides or analogs can be particularly useful where the polynucleotide is to be exposed to an environment that can contain nucleolytic activity (including endonuclease and exonuclease activity), since the modified polynucleotides can be less susceptible to degradation.

Virtually any naturally occurring nucleic acid may be sequenced including, for example, chromosomal, mitochondrial, or chloroplast DNA or ribosomal, transfer, heterogeneous nuclear, or messenger RNA. Additionally, methylated DNA and small interfering RNA (siRNA) and microRNA (miRNA) can be sequenced. RNA can be converted into more stable cDNA through the use of a reverse transcription enzyme (reverse transcriptase). Additionally, non-naturally occurring nucleic acids that are susceptible to enzymatic synthesis and degradation may be used in embodiments of the present invention.

Methods for preparing and isolating various forms of nucleic acids are known. See for example, Berger and Kimmel, eds., *Guide to Molecular Cloning Techniques*, Academic Press, New York, N.Y. (1987); and Sambrook, Fritsch and Maniatis, eds., *Molecular Cloning: A Laboratory Manual*, $2^{nd}$ ed., Cold Spring Harbor Press, Cold Spring Harbor, N.Y. (1989). However, embodiments of the present invention are not limited to a particular method for the preparation of nucleic acids.

Figure 1:
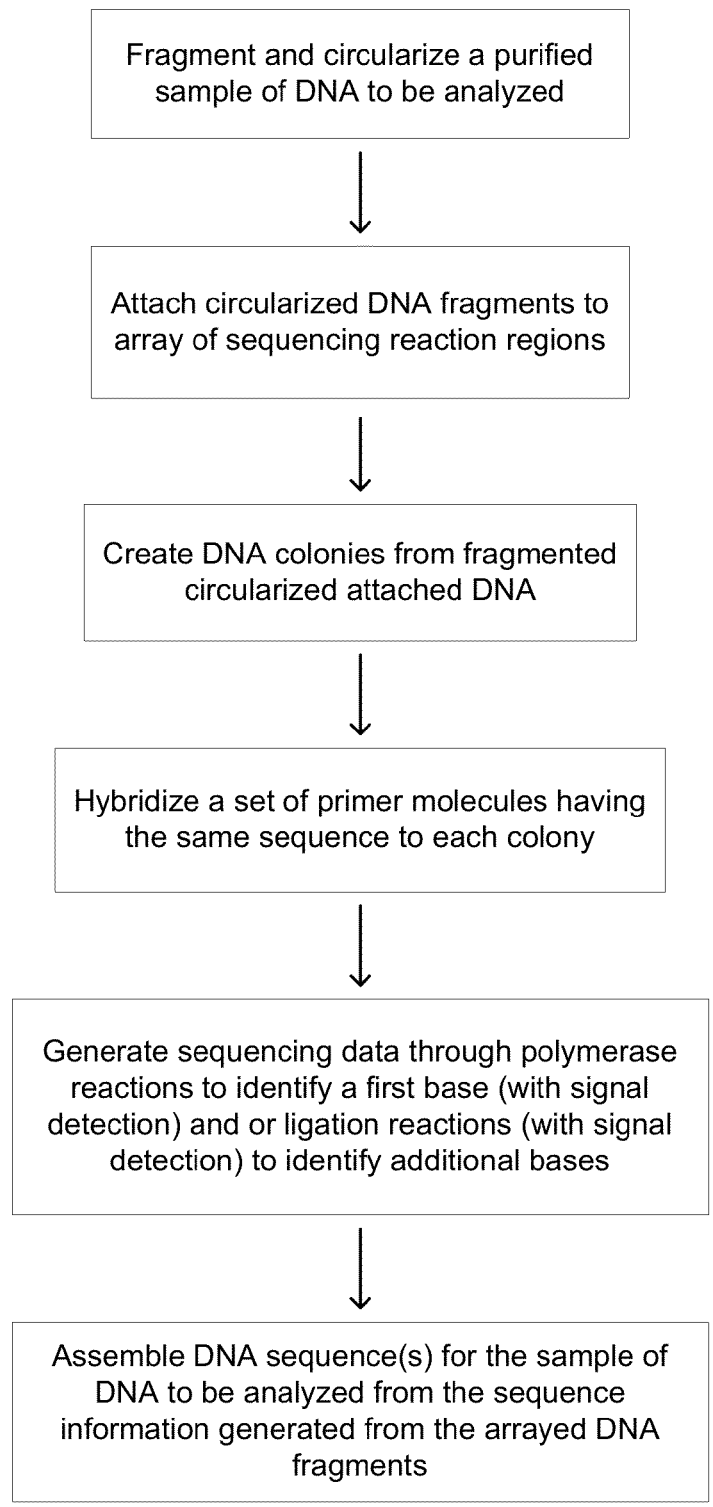
FIG. 1 provides a flow diagram for a sequencing process.

FIG. 1 outlines a nucleic acid sequencing strategy according to embodiments of the invention. In FIG. 1, a sample of DNA to be sequenced is obtained. Typically the sample will be from a living organism and will contain long polymers of DNA (DNA strands). The sample containing DNA polymers to be sequenced is purified and fragmented into smaller polymers. Fragmentation is accomplished, for example, through mechanical shearing processes and or through the action of restriction and or nuclease enzymes. Individual DNA fragments are circularized through the ligation of a double-stranded adaptor that is capable of circularizing one strand of a double-stranded DNA fragment. The double-stranded adaptor optionally comprises a nick or a gap that has an attached functional group that is capable of attaching to a substrate surface. The circularized DNA is attached to an array of sequencing reaction regions. The sequencing reaction regions comprise regions to which reagents are provided and which can be interrogated using one or more detection devices (sensors). In general, monitoring of nucleic sequencing reactions is accomplished using electronic detection, electrochemical detection, optical detection, and or a combination thereof. In one embodiment of the invention, one circularized DNA is attached in one sequencing reaction region. DNA colonies are then created by replicating the closed circle strand of the circularized DNA molecule at least ten times to form a DNA concatemer. In general, a concatemer is a DNA molecule that contains a plurality of copies of the same DNA sequences linked in series.

Continuing with FIG. 1, a set of primer molecules in which each member of the set has the same sequence is hybridized to each concatemer. Optionally, the primer molecules are exonuclease resistant primer molecules. In a first embodiment, cyclic polymerase-exonuclease reactions are performed to generate amplified reaction products that are detected and the identity of a plurality of bases of a DNA concatemer are determined. In additional embodiments, non-natural oligomers are used to determine sequencing information. Optionally, sequence information is then generated for the first base downstream of the primers using a polymerase reaction and detecting the amplified reaction product optically or electrically. The identified first base downstream of the primers is then removed (having been added by the polymerase reaction) and sets of DNA oligomers comprising this first identified base are then specifically ligated to the primer molecules. In the alternative, no separate sequence information is generated for the first base downstream of the primers and a set of oligomers are then specifically ligated to the primer molecules. The identities of two or three bases of the DNA molecule to be sequenced are determined. DNA sequence information is assembled for the DNA molecule to be sequenced from the sequence information obtained from the individual concatemers. In general, functions such as gathering and analyzing data are performed by a computer. A computer is optionally used not only to direct the addressing and monitoring of the reaction regions of the array, but also to provide reagents to the array from fluidically coupled reservoirs.

In general, exonuclease resistant primer molecules are nucleic acid molecules that cannot be digested by an exonuclease enzyme. In general, exonuclease resistant primers contain at least one exonuclease resistant nucleotide. The exonuclease resistant nucleotide is typically located at the 3' end of the primer. The exonuclease resistant primer is optionally created in situ, meaning that a primer that is not exonuclease resistant is hybridized to the DNA colonies and then an exonuclease resistant nucleotide is added to the primer.

Figure 2:
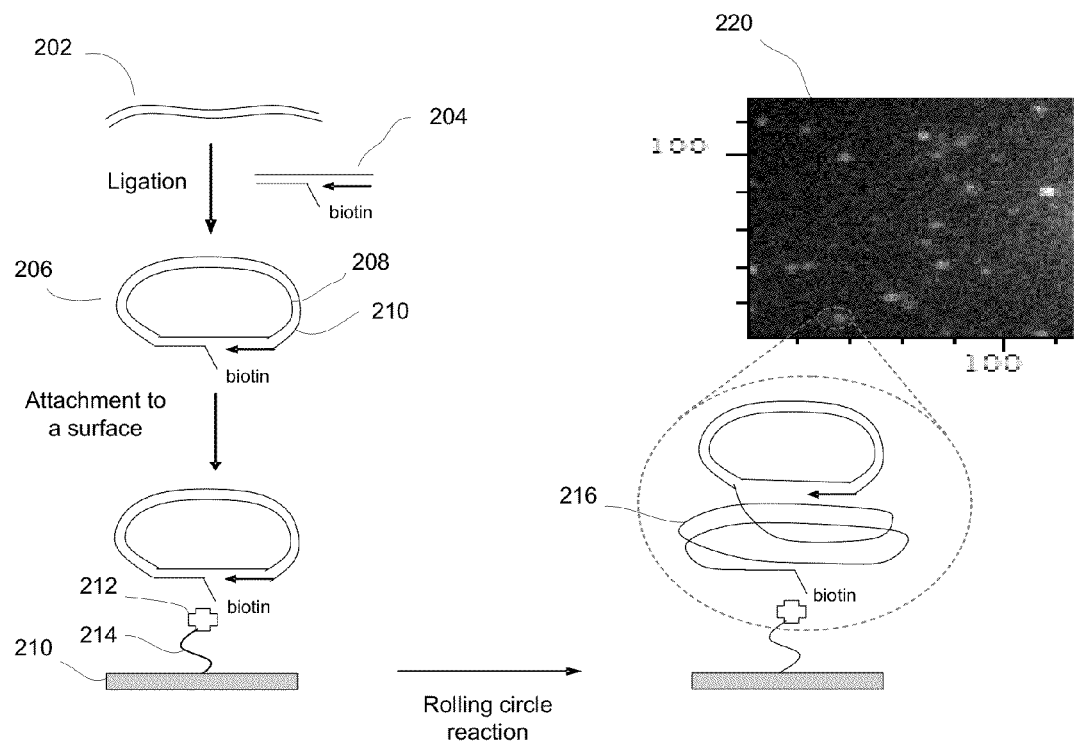
FIG. 2 shows the creation of DNA colonies from single DNA molecules.

FIG. 2 shows the creation of DNA colonies from DNA molecules. As described with reference to FIG. 1, the DNA molecules typically are fragments of a larger DNA molecule to be sequenced from a sample. The DNA molecules to be circularized are generally in the size range of between 20 nucleotides to 10 kb in length, 25 nucleotides to 5 kb, or 30 to 500 nucleotides. In FIG. 2, a single DNA molecule 202 is ligated with an adaptor 204. In general, adaptor 204 is a double stranded DNA fragment comprising a nick or a gap and a functional group capable of attaching to a substrate surface that is capable of being ligated to other DNA fragments. There are alternative ways to accomplish the circularization of a single strand DNA using a single strand specific ligase enzyme. Different DNA ligases typically have different properties and use different substrates or cofactors. Additional information is available from, for example, New England Biolabs (Ipswich, Mass.). An adaptor allows a specific sequence anchor which can be used for recognition as well as ligation. An example adaptor is 56 bp long, having an overhang "T" at each of the 3' ends and a phosphate at each of the 5' ends. The 5' phosphate facilitates ligation. There is a gap in one of the strands in the example adaptor and the 5' end of the gap is modified by a biotin group or a amine group, which is used for surface attachment. The 3' end of the gap is exonuclease resistant and can be extended by DNA polymerase but not digested by exonuclease. After a ligation reaction, the DNA sample is treated with 3' to 5' exonuclease to remove the unligated linear DNA or DNA that has an open 3' end (that is not exonuclease resistant). After the nuclease treatment, only DNA molecules with nuclease-resistant 3' ends are left and the DNA is double-stranded with one strand being a close circle and the other having gap in the adaptor region. When the DNA is used for DNA polymerization reactions, the closed circle DNA is used as a template and non-closed circle DNA is used as primer to copy the close circle DNA starting from the exonuclease resistant 3' end. Because the template is circular, the resulting DNA copy will be a concatemer with many copies of the sequence that is complementary to the circular template. The polymerization reaction is called rolling circle amplification (RCA). The polymerization reaction can be performed in solution phase or on a surface if the DNA molecules are first attached to a surface through biotin-avidin binding or covalent attachment through the 5' amine modification, for example. The product of RCA is a long single stranded DNA, but due to partial hybridization within the molecule, the long DNA looks globular under an optical imaging system. The ligation in the present embodiment is based on single base "A" overhang in the target molecule and single base "T" overhang in the adaptor. In general, adaptor can be attached to the target fragment either by sequence specific attachment using restriction digestion and then ligation, or by general blunt end ligations. The adaptor having the designed sequence can generate an overhang region (after treatment) to allow circularization. In this embodiment featuring a surface-bound avidin 212, the adaptor 204 functional group is a biotin. Surface-bound avidin variants, such as streptavidin or neutravidin, are also compatible with the biotin functional group. Other useful functional groups for surface-attachment include (depending on the surface chemistry chosen), for example, amine, thiol, carboxyl, and azido groups. The adaptor 204 is ligated to the DNA molecule 202 forming a circularized double-stranded DNA 206 having a closed circle strand 208 and a non-circularized strand 210. The circularized DNA molecule 206 is attached to a substrate 210. Typically, the substrate 210 has an array of reaction regions on a surface to which DNA molecules are attached. For simplicity, only one region is shown. In this example, the substrate presents an avidin 212 that is attached to the substrate via a flexible linker molecule 214. In this embodiment, the flexible linker molecule is terminated with functional groups that can react with amines on the avidin. In general useful flexible linker molecules include polyethylene glycols (PEGs). The circularized DNA 206 is attached through the substrate 210 surface through, for example, a biotin-avidin interaction. Rolling circle amplification is performed to create a concatemer of DNA 216. The arrow in FIG. 2 indicates the RCA initiation point, an exonuclease resistant 3' end at the gap. DNA colonies are formed by replicating the closed circle strand of a DNA molecule for more than 10 times to form a DNA concatemer. The size of the replicons created is time dependent, so that longer times mean more replicons. Typically, a useful number of replicons is between and including 2 replicons and 100 replicons, although other numbers can be used, such as a number between and including 4 and 100 replicons, 7 and 100 replicons, 10 and 100 replicons, 10 and 75 replicons, and 10 and 50 replicons.

In general, a DNA colony is a DNA molecule that contains at least 2 copies of a DNA sequence linked in series. A DNA colony can comprise 2 to 100 copies of a DNA sequence linked in series, although more typically the colony has at least 4 replicons. Other numbers are possible, such as, 7 and 100 replicons, 10 and 100 replicons, 10 and 75 replicons, and 10 and 50 replicons. DNA colonies are typically derived from a pool of immobilized single DNA molecules that have been collected from a biological sample, are more than 50% double-stranded, have a common sequence segment among the DNA molecules, contain a closed circle strand and a strand that is open or can be opened biochemically to generate a nick or a gap. In one embodiment, the DNA colonies contain exonuclease resistant bases to prevent exonuclease digestion. For polymerase incorporation, there can be as few as one base at the 3' end that is exonuclease resistant when enzyme that has an exonuclease activity is used, for example, Phi29 DNA polymerase. However, exonuclease resistance is not required when enzyme that does not have 3' to 5' exonuclease activity, such enzymes include exonuclease-free DNA polymerases, such as Bst DNA polymerase large fragment, exo-minus Vent DNA polymerase are used. Exonuclease resistant bases are chemically added when the adaptor is synthesized and it is also possible to add exonuclease resistant bases enzymatically prior to RCA reaction, or before the use of exonuclease-plus DNA polymerase.

In some embodiments, the DNA colonies are formed directly on a sensor array, in which the array is an array of reaction regions that are capable of being probed by sensors and the colonies are formed in the reaction regions. In FIG. 2, the image 220 shows fluorescent images of DNA colonies after hybridization of a set of primers having the same sequence to multiple sites on the DNA colony and single base extension from the primers using fluorescein-labeled dGTP. The magnification in image 220 is 50× and the excitation source is a halogen lamp that is filtered with a fluorescein-compatible excitation and emission filter set (FITC). The FITC excitation is around 494 nm and emission is around 518 nm. To generate the image in image 220, RCA reaction was performed inside a silicon well, followed by washing and hybridization with a primer that was complementary to the RCA DNA product (RC6 primer), a reaction solution (comprising Klenow DNA polymerase, dTTP, and Fluorescein-dGTP) was added to the well to extend and label the DNA colonies, and the well was washed to remove unused reactants. One of numerous resulting bright spots on image 220 is circled. Sequencing reactions are performed using the DNA colonies according to embodiments of the invention described herein.

Figure 3:
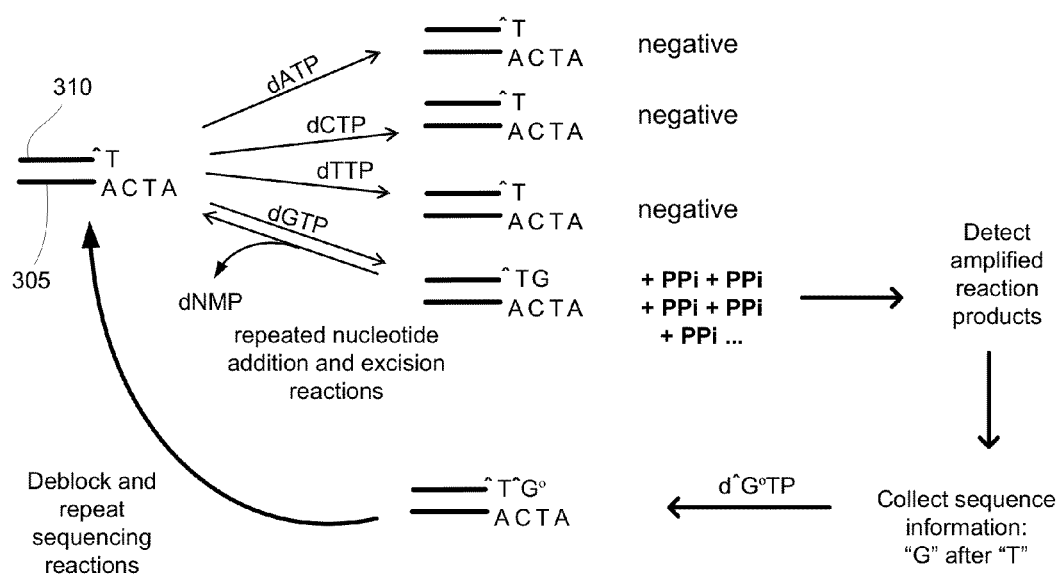
FIG. 3 outlines a general nucleic acid sequencing method using the chemical amplification of nucleic acid synthesis reaction products and the detection of amplified reaction products.

FIG. 3 diagrams a method for providing amplified chemical signals and sequencing data for nucleic acid sequencing reactions that can be used, for example, with DNA colonies to create signals from sequencing reactions that are chemically amplified in two ways. In FIG. 3, a DNA molecule to be sequenced 305 is primed with a primer 310 that is terminated with an exonuclease resistant nucleotide which, in this example, is a thymine (exonuclease resistance being indicated in FIG. 3 with a "*"). In general, exonuclease resistant primers contain at least one exonuclease resistant nucleotide. The chemical products resulting from the incorporation of a complementary dNTP (a deoxynucleotide triphosphate, e.g., dATP (deoxyadenosine triphosphate), dCTP (deoxycytidine triphosphate), dGTP (deoxyguanosine triphosphate), or dTTP (deoxythymidine triphosphate), for example) or dNTP analog, into a nucleic acid strand to be sequenced 305 are amplified through the repeated addition and excision of the next complementary nucleotide onto the priming sequence 310. In one embodiment, individual test reactions are performed using one of four dNTPs and a determination is made regarding the next complementary nucleotide in the nucleic acid to be sequenced. In general, a test reaction comprises a polymerase, an exonuclease, and a nucleoside polyphosphate such as deoxynucleoside triphosphate (dATP, dCTP, dTTP, or dGTP) or a nucleoside oligophosphate having four to six phosphates or a labeled nucleoside analog (a labeled nucleoside oligophosphate having three to six phosphates). Labels in this embodiment include redox labels that are redoxigenic, such as aminophenyl, hydroxyphenyl, or napthyl groups attached to a terminal phosphate of the nucleoside oligophosphate that become redox active upon the removal of phosphate groups. In general, a redoxigenic label is a label that becomes redox active upon its removal from the polyphosphate nucleoside after the incorporation of the labeled nucleoside into a nucleic acid molecule. The redoxigenic label may undergo further reaction after incorporation-related cleavage from the nucleoside, such as the removal of phosphate or pyrophosphate groups, before becoming redox active. After incorporation of the redox labeled nucleoside polyphosphate, phosphate groups are removed from the label using a phosphatase enzyme. The released redoxigenic label is detected electrochemically and or using redox cycling techniques.

A complementary nucleoside is incorporated into the growing DNA molecule (primer strand) 310 through the action of a polymerase enzyme. Typical useful polymerase enzymes include DNA polymerases, such as for example, $E. coli$ DNA polymerase I and the commercially available 9 N and Therminator DNA polymerases (available from New England Biolabs, Inc., Beverly, Mass.). Thus, for example, where there is a cytosine on the strand to be sequenced 305, a guanine will be incorporated, where there is a thymine, an adenosine will be incorporated, and vice versa. If a nucleoside triphosphate is incorporated into the growing strand 310 in the test reaction, then a pyrophosphate ion (i.e., a pyrophosphate, PPi, or $P_2O_7^{-4}$) or labeled pyrophosphate is released. Oligophosphates are broken into smaller phosphate units using a phosphatase enzyme. In an amplification reaction, an exonuclease is used to remove the incorporated nucleoside monophosphate ($dNMP^{-2}$), allowing another complementary nucleoside triphosphate to be incorporated and a second PPi to be released. Repetition of these addition and excision reactions provides amplification of reaction products. Thus, a positive test reaction (i.e., the detection of chemically amplified products) indicates that the base on the template DNA strand to be sequenced 310 immediately after the priming base (the 3' base) of the primer strand 310 is complementary to the test base (the one of four dNTPs that was used in the synthesis and deconstruction reaction). To sequence the next base on the template, the first identified base on the primer strand 310 is filled or replaced with a nuclease-resistant blocking nucleotide (3' blocking is indicated with a "o" in FIG. 3) (that is the nucleotide that has been identified) that then becomes the priming base for the next test reaction after deblocking. The blocking functionality on the nucleotide is optional. In general, blocking nucleotides prevent further nucleic acid synthesis by blocking the addition of a nucleic acid to the 3' end of the nucleic acid molecule. Blocking functionality is created, for example, by the modification of the 3'-OH with a non-natural group, such as for example, the creation of a 3'-OR where R is azidomethyl, allyl, or O-nitrobenzyl. Nuclease-resistant blocking nucleosides are, for example, ribonucleosides or other modified nucleosides and are modified from natural nucleosides in at least two regions conferring both blocking and nuclease resistance functionality. A variety of polymerases are available that can incorporate ribonucleotides or modified nucleosides into DNA, such as for example, the commercially available Therminator DNA polymerase (available from New England Biolabs, Inc., Beverly, Mass.). See also, for example, DeLucia, A. M., Grindley, N. D. F., Joyce, C. M., *Nucleic Acids Research*, 31:14, 4129-4137 (2003); and Gao, G., Orlova, M., Georgiadis, M. M., Hendrickson, W. A., Goff, S. P., *Proceedings of the National Academy of Sciences*, 94, 407-411 (1997). Exemplary exonuclease resistant bases include alpha-phosphorothioate nucleosides, and exemplary nucleases that cannot digest these resistant bases include exonuclease III. Some polymerase enzymes possess exonuclease activity. Additional examples of exonuclease resistant blocking nucleotides are found, for example, in U.S. patent application Ser. No. 12/823,995, entitled "Nucleotides and Oligonucleotides for Nucleic Acid Sequencing," filed Jun. 25, 2010. Reactions in which no significant amount of product is detected indicate that the test reaction provided a nucleotide that was not complementary to the next base of the nucleic acid to be sequenced. After addition of the next known complementary nucleotide to the primer 210, the primer 210 is deblocked through removal of the 3' blocking group and the identity of the next complementary nucleotide is determined by repeating the reactions as described above.

Blocking nucleotides that have been modified at the 3' position with, for example, 3'-azidomethyl or 3'-allyl, are cleaved chemically to deblock the nucleotide, using for example, TCEP (tricarboxylethylphosphine) for 3'-azidomethyl and aqueous Pd-based catalyst to remove 3'-allyl group, and 3'O-nitrobenzyl blocking groups are cleaved photochemically. T Sequence information obtained from a plurality of concatemers is stitched together using a computer to obtain the sequence of the full DNA molecule. DNA sequence information is assembled by examining the overlapping sequence outputs. To assemble the sequencing information into a genome information, the sequence information is, typically, 10× to 50× redundant (or called coverage, meaning to sequence the DNA 10 to 50 times for each given region). A computer program is used to assemble the sequence fragments into a full length sequence. For a read-length of 35 nucleotide long, the coverage is about 30×. For a read-length of greater than 100, the coverage is about 10×. Statistics tools may also be used to determine the sequencing for ambiguous information. Open-source sequence assembly software is available, for example, as A Modular, Open-Source whole genome assembler (AMOS) (from the University of Maryland).

Detection of nucleic acid sequencing reactions is performed, for example, optically, electronically, and or electrochemically. Typically sensors are formed as an array of individually addressable sensors. The regions probed by the sensors (sensor regions or sensing regions) in the array are functionalized to allow attachment of molecules. The sensing regions become reaction regions in which DNA molecules to be sequenced are immobilized. Typically one DNA molecule is immobilized in each region. The immobilization of one DNA molecule per reaction region can be accomplished, for example, by diluting the sample of DNA so that statistically one DNA molecule is attached in one region. Alternately, the number of attachment sites for DNA molecules can be reduced. Signals from reaction regions having more than one DNA molecule attached or no DNA molecules attached are ignored. The immobilized DNA molecules are converted to DNA colonies.

Figure 4:
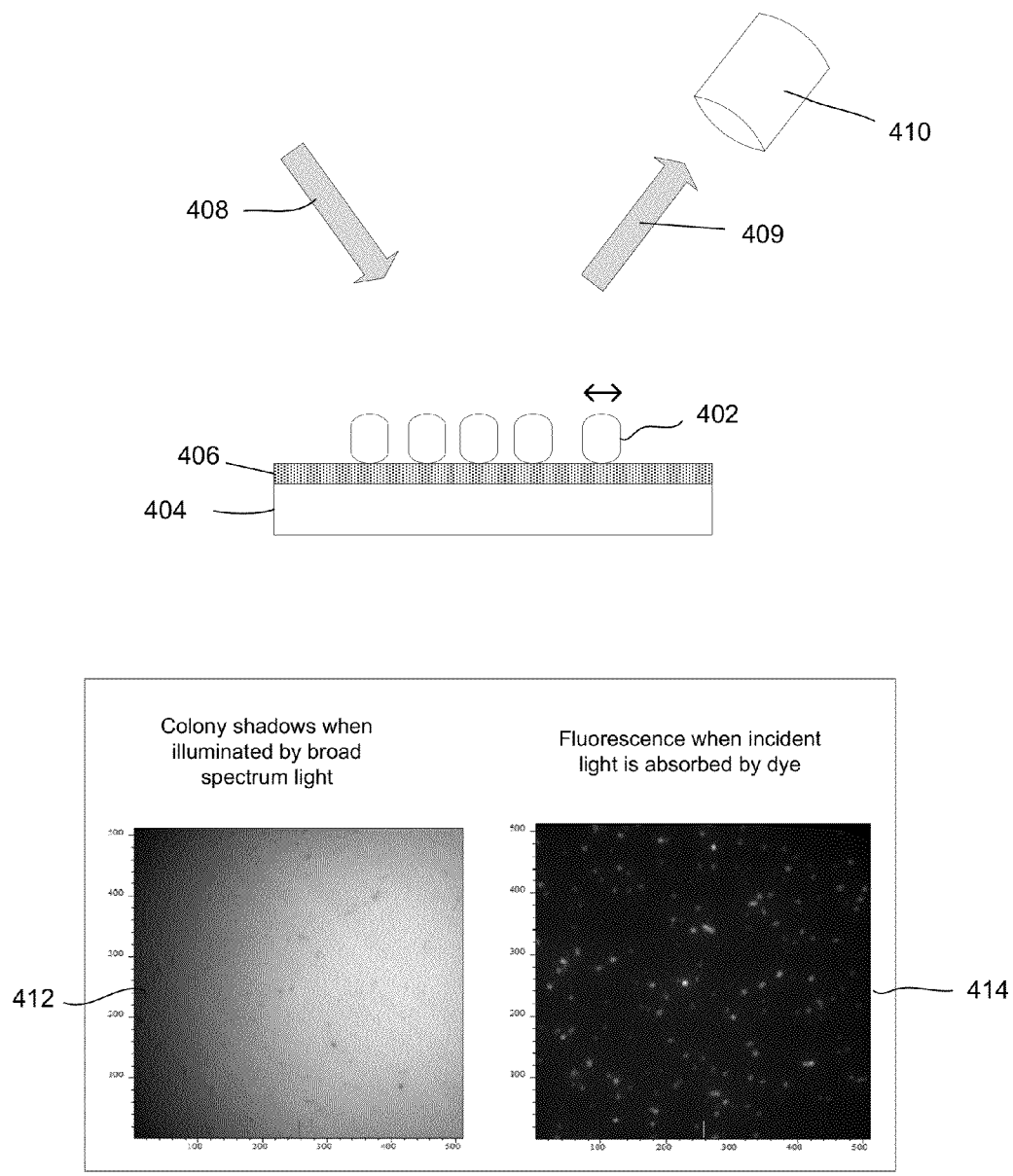
FIG. 4 demonstrates refractive index- and fluorescence-based detection of DNA colonies.

FIG. 4 provides a scheme of a detection method for DNA sequencing reactions based on surface refractive index changes. In FIG. 4, individual DNA colonies 402 comprising a concatemer of DNA are attached to a substrate 404 having a metal coating 406. Typical substrates include glass, silicon, polymers, and carbon-based materials such as graphite, grapheme, or diamond, and semiconductor surfaces such as gallium arsenide. Typical metals include gold, platinum, palladium, aluminum, and silver. Incident light 408 moves through the solution (not shown) above the DNA colonies 402, impinges on the metal coating 406 at a first angle, and is reflected toward detector 410 at a second angle (reflected light 409). A local refractive index change causes the second angle, the angle of reflection, to change thereby moving the reflected light to a different position with respect to the detector 410. Localized changes in the refractive index of a solution (not shown) above the metal 406 coated substrate 404 cause colony shadows when illuminated by broad spectrum light as shown in image 412. A phase contrast microscope is used to detect the refractive index changes. In image 412, the substrate was glass and the metal was aluminum. A halogen lamp without a filter and a deep cooling CCD camera was used. A 50× objective was used with a Nikon eclipse E2000 microscope. A change in refractive index is caused by a local chemical composition change and or a local density change from for example, the local heating produced by the hydrolysis of nucleotide triphosphates. Nucleic acid sequencing reactions using un-labeled nucleotides according to embodiments of the invention are optically detected based on surface refractive index changes. Image 414 shows the fluorescence observed when DNA colonies 402 are labeled with cy5 dye and the incident light is absorbed by the dye (FTC excitation and emission filters were used).

Figure 5A:
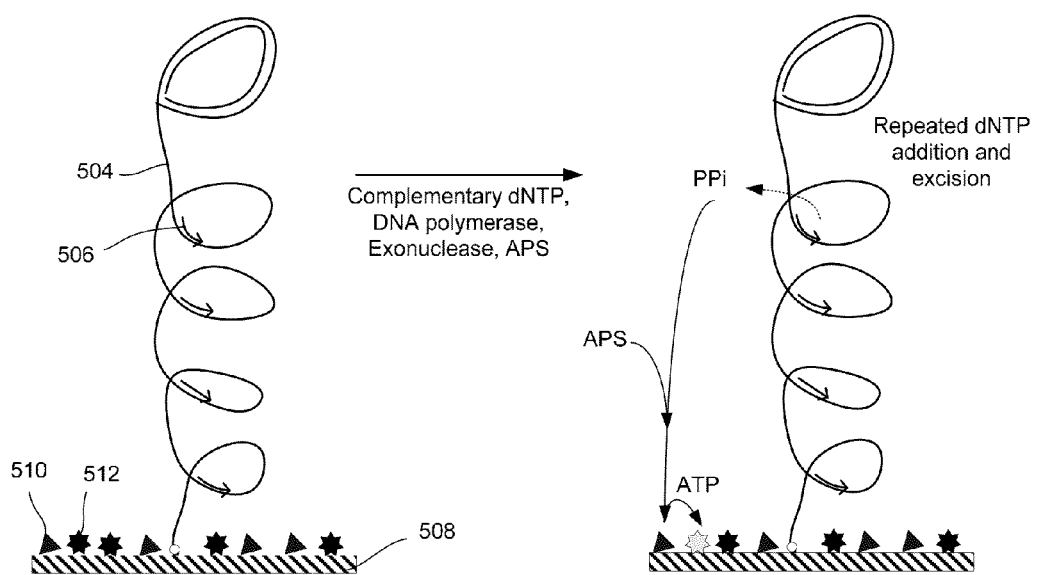
FIGS. 5A-B describe signal generation schemes useful for the optical detection of DNA sequencing reactions.

FIG. 5A presents a scheme adapted to sequence DNA using optical detection. In FIG. 5A, a concatemer of DNA 504 is shown having 4 repeating sections having the same DNA sequence for simplicity, however larger numbers of repeating sections are possible, such as 7 to 100 repeating sections of a DNA sequence. The concatemer 504 is primed with primer molecules 506 having the same sequence. Optionally, the primer molecules 506 are exonuclease resistant primer molecules. The concatemer 504 is attached to a substrate 508. In some embodiments, the substrate 508 is an optical window such as, for example, the transparent support of FIGS. 7A-B or a transparent substrate optically coupled to a light detector. Materials for the transparent substrate include, glass, quartz, a thin dielectric such as $SiO_2$, siliconoxynitride, indium tin oxide, and or a transparent plastics. The substrate 508 typically is part of a larger array comprising reaction regions capable of being monitored optically and having an immobilized DNA concatemer. Sulfurylase 510 and luciferase 512 enzymes are attached to substrate 508. Test reactions are performed by providing a solution comprising a polymerase, an exonuclease, an unlabeled deoxynucleoside triphosphate, and APS (adenosine 5'-phosphosulfate). For the test reaction comprising the dNTP (or a nucleoside or nucleoside analog oligophosphate having four to six phosphate groups) that is complementary to the first base of the concatemer 504 immediately downstream of the primer molecule, a signal is obtained. Through the cyclic addition and excision of the next complementary dNTP (or nucleoside analog), PPi is generated. Oligophosphates are broken into smaller phosphates using a phosphatase enzyme. The PPi reacts with APS and sulfurylase 510 to generate ATP. The ATP that is generated reacts with luciferase 512 to generate light that is then detected through a coupled optical detector (not shown).

Figure 5B:
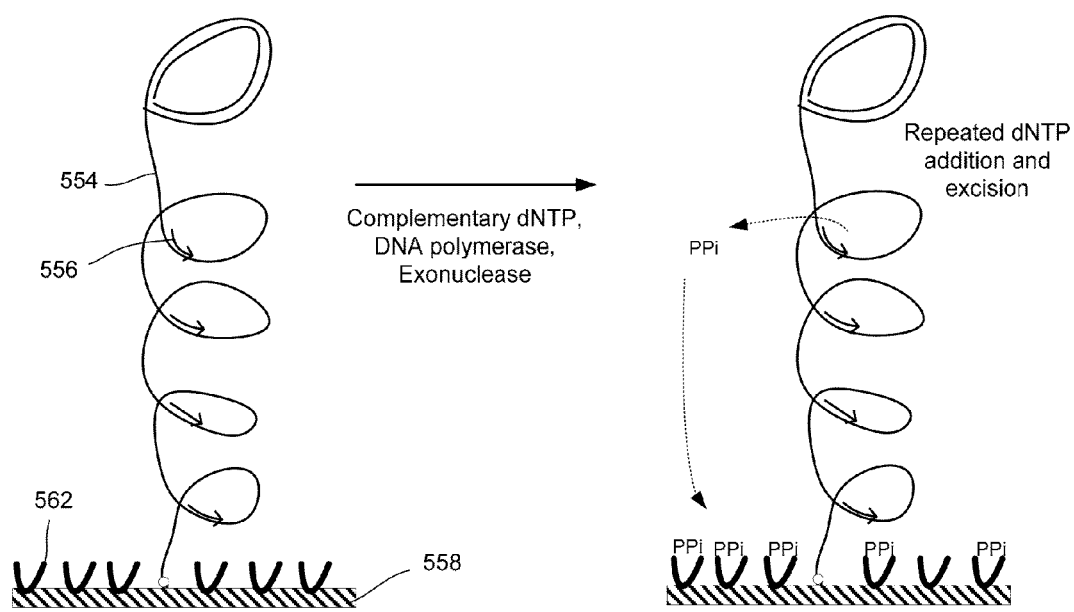

FIG. 5B presents an additional scheme adapted to sequence DNA using optical detection. In FIG. 5B, a concatemer of DNA 554 is shown having 4 repeating sections having the same DNA sequence for ease if illustration, however larger numbers of repeating sections are possible, such as 7 to 100 repeating sections of a DNA sequence. The concatemer 554 is primed with primer molecules 556 that have the same sequence. Molecules 562 capable of binding PPi and emitting light after binding PPi are attached to the substrate 554. Molecules 562 that are capable of binding PPi and emitting light after binding PPi include, for example, those found in Kim, S. K, et al, *Acc. Chem. Res.*, 42(1), 23-31 (2009). Alternatively, the PPi capture molecules 562 have a covalently attached fluorescent molecule that is displaced when PPi binds to the capture molecule 562. When the covalently attached fluorescent molecule is bound by the PPi capture molecule 562 its fluorescence is quenched. The covalently attached fluorescent molecule is capable of fluorescing upon displacement from the capture region of PPi capture molecule 562. The PPi capture molecule 562, is for example, found in Kim, S. K, et al, *Acc. Chem. Res.*, 42(1), 23-31 (2009). In additional embodiments, the PPi capture molecules 562 are attached to the primer molecules 556. Attachment is accomplished with standard EDC (1-ethyl-3-(3-dimethylaminopropyl)carbodiimide) chemistry or other coupling chemistry using molecules modified by groups such as, for example, amine, carbosyl, thiol, and aldehyde groups. The substrate 558 typically is part of a larger array comprising reaction regions capable of being monitored optically and having an immobilized DNA concatemer. In some embodiments, the substrate 558 is an optical window such as, for example, the transparent support of FIGS. 7A-B or a transparent substrate optically coupled to a light detector. Test reactions are performed by providing a solution comprising a polymerase, an exonuclease, and an unlabeled deoxynucleoside triphosphate (or a nucleoside tetra- or higher oligo-phosphate or dNTP analog). For the test reaction comprising the dNTP (or dNTP analog) that is complementary to the first base of the concatemer 554 immediately downstream of the primer molecule, a signal is obtained. Through the cyclic addition and excision of the next complementary dNTP (or a nucleoside tetra- or higher oligo-phosphate or dNTP analog), PPi is generated. The PPi that is generated from the positive test reaction is detected upon binding to the PPi capture molecule 562.

Figure 6:
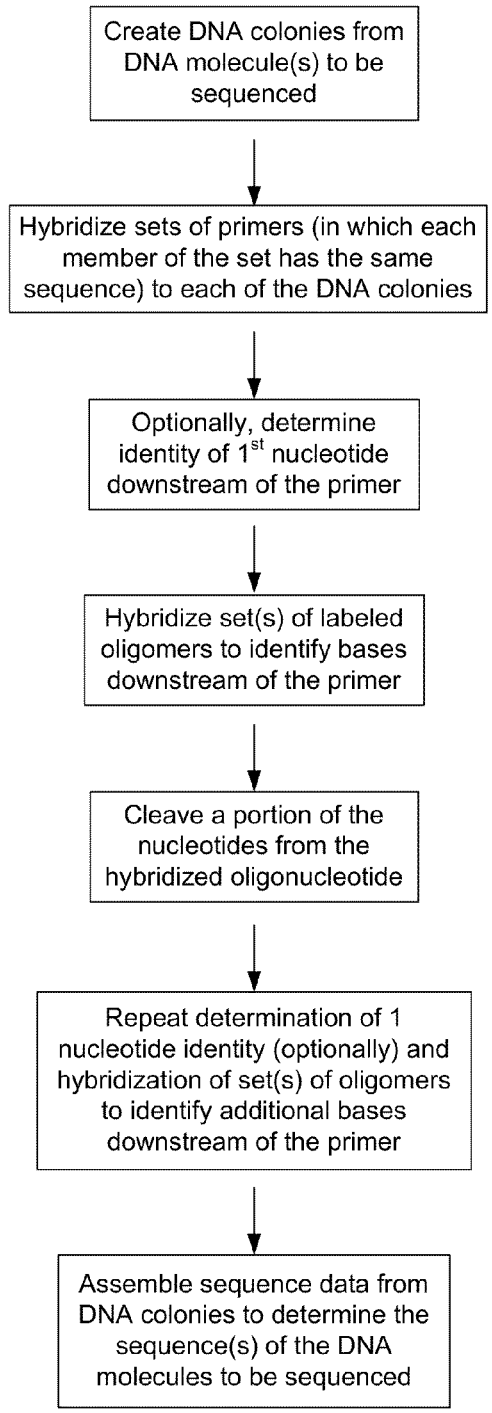
FIG. 6 provides nucleic acid sequencing methods that employ DNA colonies and non-natural oligonucleotides.

FIG. 6 provides additional sequencing methods that use non-natural oligonucleotides to determine sequence information from DNA colonies. In FIG. 6, large DNA molecules to be sequenced are broken into smaller polymers. The smaller polymers are used to create DNA colonies that are attached to the sensor regions of an array of sensors. Optionally, one colony is attached in one sensor region. A set of primer molecules in which each member of the set has the same sequence is hybridized to each of the DNA colonies. Optionally, the primer molecules are exonuclease resistant primer molecules. Exonuclease resistant primer molecules have at least one exonuclease resistant nucleotide. The exonuclease resistant nucleotide is typically located at the 3' end of the primer. The exonuclease resistant primer is optionally created in situ, meaning that a primer that is not exonuclease resistant is hybridized to the DNA colonies and then an exonuclease resistant nucleotide is added to the primer. Optionally, sequence information is then generated for the first base downstream of the primers using polymerase reactions to insert a complementary nucleotide (dNTP) or nucleotide analog. Reaction products are detected optically (using fluorescently labeled dNTPs and fluorescence detection of an incorporated fluorescently-labeled complementary nucleotide) or electrically (detecting amplified pyrophosphate reaction products from the incorporation and excision of a complementary nucleoside polyphosphate, or the redoxigenic label from a redox labeled dNTP). The first base downstream of the primer is then removed.

According to a first method, the first base is identified using the polymerase reactions and then four sets of DNA oligomers (labeled "Option 1" in FIG. 6) are applied to the DNA colonies under conditions that allow the complementary oligomer to hybridize to the DNA colony and be ligated to the primer molecule after hybridization. Four sets of oligomers, as shown in FIG. 6, Option 1, are allowed to react sequentially (one set at a time) until a signal is detected for the hybridized ligated complementary oligonucleotide (oligomer) to identify the second and third bases downstream of the primer molecule. The four sets of oligonucleotides determine the 16 possible base combinations for the two unknown bases. There are 16 different oligonucleotides in each set. In a sequencing run as described here, the identity of three bases downstream of the primer molecule are determined. The third nucleoside of the oligonucleotides shown in FIG. 6, Option 1, is a nuclease-resistant nucleotide, as indicated by a "^" in FIG. 6. In FIG. 6, "u" represents a universal nucleoside and N represents an oligonucleotide having one of the four bases. Oligonucleotides representing all four bases for N are present in each set. The numbers 1-4 are different detectable labels. Labels are, for example, fluorescent labels, such as fluorescein, rhodamine 6G (R6G) and other rhodamine derivatives such as carboxyrhodamine, TAMRA, BODIPY, and or cyanine dyes such as Cy5, Cy3. The detection of the label determines the identity of the second complementary base. In an alternate embodiment, the second nucleotide of the oligonucleotides in a set is the same oligonucleotide and the fluorescent label indicates the identity of the third nucleotide. Fluorescent labels are attached to one of the universal nucleotides or other nucleotides that are removed after ligation. The identity of the third complementary base is determined from the set of oligonucleotides used. In the alternate embodiment, the identity of the second complementary base is determined from the set of oligonucleotides used. The identity of the complementary oligonucleotide is determined by washing reagents from the vicinity of the DNA colony and detecting the presence and location (in the array) of the fluorescent labels that are attached to the complementary oligonucleotides. After the identity of the complementary oligonucleotide is determined, the universal nucleotides are digested from the ligated oligonucleotide, leaving three bases of the oligonucleotide. The elements of identifying a base proximate to the (now extended) primer and applying four sets of labeled oligonucleotides are repeated to determine the identity of the desired number of bases of the DNA molecule to be sequenced. Results from a plurality of concatemers are stitched together using a computer to obtain the sequence of the full DNA molecule (for a DNA molecule that was broken into smaller sections for sequencing).

A second option employing non-natural oligonucleotides to determine sequence information for DNA colonies uses the set of oligomers shown as "Option 2" in FIG. 6. DNA colonies are created and primed. The primer is nuclease resistant. Sequence information is then generated for the first base downstream of the primers using polymerase reactions to insert a complementary nucleotide (dNTP). Reaction products are detected optically (using fluorescently labeled dNTPs and fluorescence detection of an incorporated fluorescently-labeled complementary nucleotide) or electrically (detecting amplified pyrophosphate reaction products from the incorporation and excision of a complementary nucleotide, or the redoxigenic label from a redox labeled dNTP). The first base downstream of the primer is then removed. A set of non-natural oligonucleotides is applied to the primed DNA colonies under conditions that allow complementary oligonucleotides to hybridize to the DNA colonies. The hybridized complementary oligonucleotides are ligated to the primer. Unhybridized oligonucleotides are washed from the DNA colonies and a signal is detected from the ligated complementary oligonucleotide. In Option 2 of FIG. 6, N represents a nucleotide having one of the four bases, and there are 64 different oligomers in the set since both N's comprise one of four nucleosides and all for nucleosides are provided in the set for each N. The second base of each oligonucleotide is DNA resistant, as indicated by a "^" in FIG. 6. As before, "u" represents a universal nucleoside. The numbers 1-4 are different detectable labels. Labels are, for example, fluorescent labels, such as fluorescein, rhodamine 6G (R6G) and other rhodamine derivatives such as carboxyrhodamine, TAMRA, BODIPY, and or cyanine dyes such as Cy5, Cy3. The detection of the label determines the identity of the second complementary base of the DNA colony in which it is detected. Fluorescent labels are attached to one of the universal nucleotides or a nucleotide that is removed after ligation. The identity of the complementary oligonucleotide is determined by washing reagents from the vicinity of the DNA colony and detecting the presence and location (in the array) of the fluorescent labels that are attached to the complementary oligonucleotides hybridized to the DNA colony. After the identity of the complementary oligonucleotide is determined, the universal nucleotides and one base are digested from the ligated oligonucleotide, leaving the first two nucleotides of the oligomer. The identities of two bases of the DNA molecule to be sequenced are determined. The elements of identifying a base downstream of the (now extended) primer and ligating a complementary labeled oligonucleotide are repeated to determine the identity of the desired number of bases of the nucleic acid to be sequenced. Results from a plurality of concatemers are stitched together using a computer to obtain the sequence of the full DNA molecule (for a DNA molecule that was broken into smaller sections for sequencing).

A third option using non-natural oligonucleotides to determine sequence information for DNA colonies uses the set of oligomers shown as "Option 3" in FIG. 6. DNA colonies are created and primed. Four sets of oligomers, as shown in FIG. 6, Option 3, are allowed to react sequentially (one set at a time) until a signal is detected for the hybridized ligated complementary oligonucleotide to identify the second and third bases downstream of the primer molecule. The four sets of oligonucleotides determine the 16 possible base combinations for two unknown bases (second and third bases downstream of the primer molecule). The hybridized complementary oligonucleotides are ligated to the primer. Unhybridized oligonucleotides are washed from the DNA colonies and signals are detected from the ligated complementary oligonucleotides. In Option 3 of FIG. 6, N represents a nucleotide having one of the four bases. A set of oligomers comprises 16 different oligomers since N represents a nucleoside having one of the four bases and nucleotides representing all four bases are present in the set. The second base of each oligonucleotide is DNA resistant, as indicated by a "^" in FIG. 6. As above, "u" represents a universal nucleoside. The numbers 1-4 are different detectable labels coding for the second bases of the oligomers. Labels are, for example, fluorescent labels, such as fluorescein, rhodamine 6G (R6G) and other rhodamine derivatives such as carboxyrhodamine, TAMRA, BODIPY, and or cyanine dyes such as Cy5, Cy3. The detection of the label determines the identity of the second complementary base. Fluorescent labels are optionally attached to one of the universal nucleotides. The identity of the third complementary base is determined from the set used that provided the positive signal for a hybridization and ligation event. The identity of the complementary oligonucleotide is determined by washing reagents from the vicinity of the DNA colony and detecting the presence and location (in the array) of fluorescent labels that are attached to the complementary oligonucleotides hybridized to the DNA colony. After the identity of the complementary oligonucleotide is determined, the universal nucleotides and one nucleotide are digested from the ligated oligonucleotide, leaving two nucleotides of the oligomer. The identities of two bases of the DNA molecule to be sequenced are determined. The elements of applying four sets of labeled oligonucleotides and determining the identity of the complementary oligonucleotide are repeated to determine the identity of the desired number of bases of the nucleic acid to be sequenced. Results from a plurality of concatemers are stitched together using a computer to obtain the sequence of the full DNA molecule (for a DNA molecule that was broken into smaller sections for sequencing).

In methods described in FIG. 6, some options require alternative use of oligo ligation-cleavage and polymerization-cleavage reactions. However, in an alternate embodiment the oligo ligation-cleavage methods are used without the additional polymerization-cleavage reactions when the sample is sequenced by two primers which are offset by one or two nucleotides (1-2 bases longer or shorter). For example, in the case of Option 1 of FIG. 6, information obtained from one primer will have one base gap for every two bases sequenced and the gaps are filled based on information obtained using the second primer that is 1-2 bases longer or shorter.

In alternate embodiments, an internal ribonuclease-sensitive base is used instead of the nuclease resistant base. RNase HII is used as an endonuclease to cut 5' to the ribonucleotide ($3^{rd}$ position), resulting in the same structure as the exonuclease digestion (nuclease resistant at the $2^{nd}$ position). In these embodiments, cleavage occurs at the ribonuclease sensitive nucleotide.

In general, a universal base (or nucleoside) is a nucleobase analog that is capable of hybridizing non-selectively to each of the natural bases. The universal nucleoside analogs are capable of pairing with each natural base. In FIG. 6, the non-natural oligonucleotides comprise four universal nucleotides, however, other numbers of universal nucleotides are possible, such as for example, 4 to 7 universal nucleotides. Some exemplary useful universal nucleotides include 3-nitropyrrole or 5-nitroindole, and universal nucleotides bearing labels that can be used to make labeled non-natural oligonucleotides include, for example, modified 5-nitroindole with a label attached to a linker at the 3-position. In general, a label provides a detectable signal, and can be, for example, a fluorescent label. Typical useful ligase enzymes include T4 DNA ligase, *E. coli* ligase, or thermostable ligases (available, e.g., from New England Biolabs, Ipswich, Mass.). Exemplary exonuclease resistant bases include alpha-phosphorothioate nucleotides, and exemplary nucleases that cannot digest these resistant bases include exonuclease III. Additional examples of functional groups that confer nuclease resistance can be found, for example, in U.S. patent application Ser. No. 12/823,995, entitled "Nucleotides and Oligonucleotides for Nucleic Acid Sequencing," filed Jun. 25, 2010. Alternately, an RNase sensitive base at the $3^{rd}$ position is used instead of a exonuclease resistant base at the $2^{nd}$ position. RNase H II (NEB) can recognize a single ribonucleotide in a DNA oligonucleotide and cleaves 5' to the ribonucleotides, providing the same result as an 3' to 5' exonuclease digestion (to the 3' of the $2^{nd}$ base).

Typical useful polymerase enzymes include DNA polymerases with or without 3' to 5' exonuclease activities, such as for example, *E. coli* DNA polymerase I, Klenow fragment of *E. Coli* DNA polymerase I, phusion DNA polymerase, Therminator DNA polymerase, reverse transcriptase, Taq DNA polymerase, Vent DNA polymerase (all available from New England Biolabs, Inc., Ipswitch, Mass.), T4 and T7 DNA polymerases, and Sequenase (all available from USB Corporation, Cleveland, Ohio). A variety of polymerases are available that can incorporate ribonucleotides or modified nucleotides into DNA, such as for example, the commercially available Therminator DNA polymerase (available from New England Biolabs, Inc., Ipswitch, Mass.) or genetically engineered DNA polymerases. See also, for example, DeLucia, A. M., Grindley, N. D. F., Joyce, C. M., *Nucleic Acids Research*, 31:14, 4129-4137 (2003); and Gao, G., Orlova, M., Georgiadis, M. M., Hendrickson, W. A., Goff, S. P., *Proceedings of the National Academy of Sciences*, 94, 407-411 (1997). Exemplary exonuclease resistant nucleotides that can be incorporated into growing DNA strands but that are resistant to digestion by exonucleases (such as the 3' to 5' exonuclease active DNA polymerases or exonuclease I and III) include alpha-phosphorothioate nucleotides (available from Trilink Biotechnologies, Inc., San Diego, Calif.). Additionally, ribonucleotides can be incorporated into a growing DNA strand by Therminator DNA polymerase or other genetically engineered or mutated polymerases. Phi-29 DNA polymerase (available from New England Biolabs, Inc.) provides strand displacement activity and terminal deoxynucleotide transferase provides template independent 3' terminal base addition. In one embodiment exonuclease free polymerase is used in combination with Exo III exonuclease.

Figure 7A:
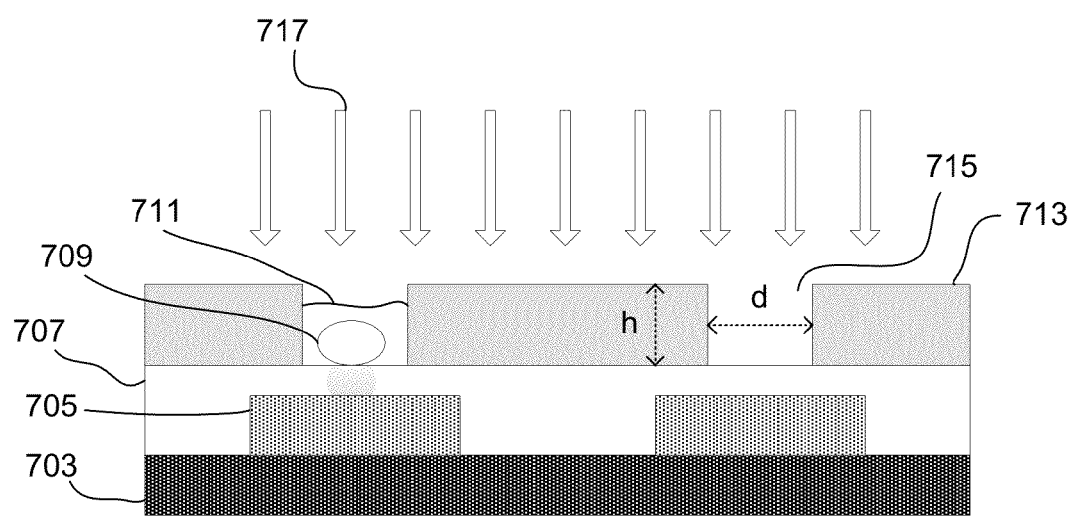
FIGS. 7A-B schematically describe two fluorescence detection devices useful for sequencing DNA.
Figure 7B:
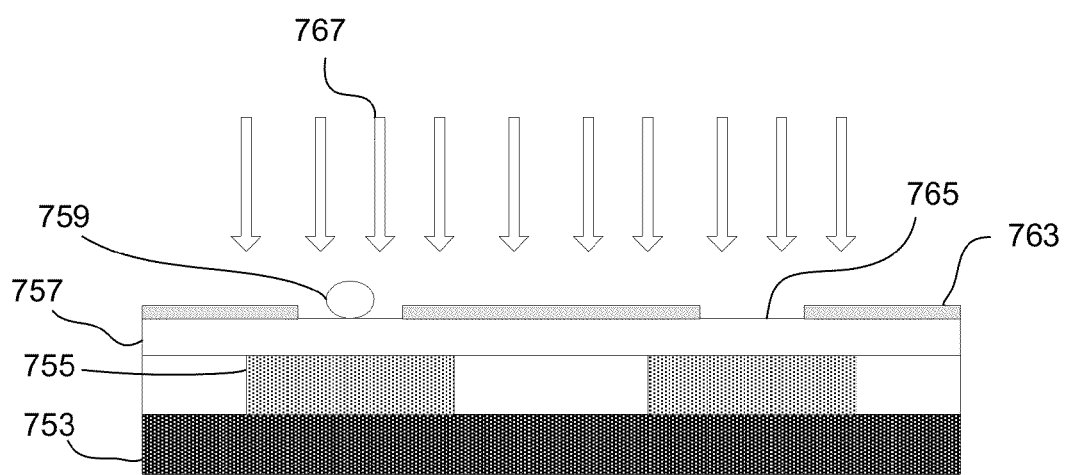

FIGS. 7A and 7B show two different optical detection devices that can be used, for example, in conjunction with the devices and methods shown and described for FIGS. 1, 2, 3, 5A-B, and 6. The devices of FIGS. 7A-B are shown for simplicity as having two different sensor-coupled detection regions, however, typically the devices will comprise many more detection regions and be arrays of detection regions. The device of FIG. 7A is typically useful for fluorescence detection. In FIG. 7A, a substrate 703 houses circuitry (not shown) operably connected to the sensor regions 705. Sensor regions 705 are, for example, SPAD (single photon avalanche diodes), CMOS-sensors, or CCD (charge-coupled device) sensors. A CMOS sensor array is an active pixel sensor array fabricated by CMOS semiconductor technology. CMOS sensor arrays typically are less expensive to make but also less sensitive and have more noise than a CCD sensor array. Single photon avalanche diodes are described, for example, in Niclass, C., et al., "Single Photon Avalanche Diode Implemented in 130 nm CMOS Technology," *IEEE Journal of Selected Topics in Quantum Electronics*, 13:4, 863 (2007). The circuitry is capable of driving and collecting sensor output from the sensor regions 705. Typically, the circuitry has the read out functions of amplification and digitization of output. The circuitry is capable of connection to a computer that collects and analyzes data. A transparent support member 707 is placed between the sensor regions 705 and serves as an attachment site for the DNA colonies 709 and any optional PPi or Pi (phosphate) binding molecules (not shown). The PPi or Pi binding molecules are optionally attached on the surface of the transparent support member 707 and in regions of transparent support member 707 that are in intimate contact with the solution 711 that serves as the vehicle for reagents for the sequencing reactions. The transparent support 707 is comprised of optically transparent materials, such as for example, glass, quartz, a thin dielectric such as $SiO_2$, siliconoxynitride, indium tin oxide, and or a transparent plastics. Optionally, the DNA colonies 709 are attached instead to the non-transparent plate 713 that creates nanowells 715 that house solution 711. The non-transparent plate 713 is comprised of a material that is inert under DNA sequencing conditions and is optionally a metal that provides surface plasmon resonance effects that can enhance fluorescence, such as, for example, gold, silver, copper, and aluminum. Light beam 717 illustrates the illumination of the optical detection device. Nanowells 715 have a width or diameter (depending on the shape of the well), labeled "d" in FIG. 7A, that is less than $\lambda/2$, where $\lambda$ is the wavelength of incident light from the light beam 717 that is used to probe the DNA sequencing reactions in the nanowells 715. Additionally, nanowells 715 are characterized by a height, "h" in FIG. 7A, that is greater than $\lambda/2$, where $\lambda$ is the wavelength of incident light from the light beam 717. This configuration does not allow zero mode light waves to reach the sensor.

In operation, the device of FIG. 7A houses DNA colonies 709 in nanowells 715 and fluorescence is generated when polyphosphate molecules are released from DNA polymerase sequencing reactions (as described herein). The PPi (or Pi) interacts with a molecule that is fluorescent upon PPi or Pi binding or alternatively, fluorescence is reduced upon PPi or Pi binding to the PPi or Pi receptor molecules. Fluorescent signal generating chelators are attached to the DNA priming molecules and or to the surface of the nanowell 715 through a linker molecule. Optionally, the DNA molecules are in solution, however surface-attachment allows the signals to be confined and concentrated.

In general, PPi or Pi ($PO_4^{2-}$) binding molecules are molecules that specifically recognize PPi or Pi. In addition to specific recognition of the PPi or Pi molecule, the PPi or Pi binding molecules are capable of providing an optically detectable signal upon PPi or Pi binding. The optically detectable signal is, for example, a fluorescent signal. The fluorescent signal can be the triggered by binding PPi or Pi or can be turned off by the binding of PPi or Pi. The PPi or Pi binding molecule is, for example, a chelating molecule that comprises a cofactor such as a metal ion, such as, $Zn^{2+}$, $Cu^{2+}$, and or $Fe^{3+}$. Additionally, the PPi or Pi recognition and signaling molecules have a surface (or molecular) attachment site. The surface attachment site is, for example, a group such as, a —$NH_2$ group, an —OH group, a halogen, a thiol, a carboxyl group, an alkyne group, an azido (—$N_3$) an aldehyde, or an —NH—$NH_3$ group. The present invention is not limited by how the chelating molecule is attached to the surface and other attachment chemistries are possible. The surface attachment site is coupled to the chelating molecule through a spacer with functional groups or a linker group and is a group, such as for example, a polyethylene glycol (PEG), polyphosphate (($PO_4)_n$), a structure such as (—C—)$_n$ which is from 1 to 100 atoms in length and can contain functional groups such as amine, hydroxyl, epoxy, aldehyde, carboxyl, and or thiol. Exemplary PPi or Pi fluorescence reporting systems are described in U.S. patent application Ser. No. 12/655,459, entitled "Solid-Phase Chelators and Electronic Biosensors," filed Dec. 30, 2009. A survey of molecules that are specific PPi chelators can be found in Kim, S. K., et al, "Chemiosensors for Pyrophosphate," *Acc. Chem. Res.*, 42, 23-31 (2009); and Kruppa, M. and Konig, B., "Reversible Coordinative Bonds in Molecular Recognition," *Chem. Rev.*, 106, 3520-3560 (2006).

FIG. 7B provides a second optical detection device. The device of FIG. 7B is typically useful for the detection of light absorption. In FIG. 7B, a substrate 753 houses circuitry (not shown) operably connected to the sensor regions 755. Sensor regions 755 are, for example, SPAD (single photon avalanche diodes), CMOS-sensors, or CCD (charge-coupled device) sensors. A CMOS sensor array is an active pixel sensor array fabricated by CMOS semiconductor technology. Single photon avalanche diodes are described, for example, in Niclass, C., et al., "Single Photon Avalanche Diode Implemented in 130 nm CMOS Technology," *IEEE Journal of Selected Topics in Quantum Electronics*, 13:4, 863 (2007). The circuitry is capable of driving and collecting sensor output from the sensor regions 755. Typically, the circuitry has the read out functions of amplification and digitization of output. The circuitry is capable of connection to a computer that collects and analyzes data. A transparent support member 757 is placed between the sensor regions 755 and the DNA colonies 759 and any PPi or Pi binding molecules (not shown). The PPi or Pi binding molecules are optionally attached to the transparent support member 757 on the section of the surface of the transparent support member 757 that is in intimate contact with the solution (not shown) that serves as the vehicle for reagents for the sequencing reactions. The transparent support is comprised of, for example, glass, quartz, a thin dielectric such as $SiO_2$, siliconoxynitride, indium tin oxide, and or transparent plastics. The non-transparent coating 763 blocks light transmission and is comprised of a material that is inert under DNA sequencing conditions and is optionally a metal, such as, for example, gold, silver, copper, and aluminum. Light beam 767 is illustrated illuminating the optical detection device.

In operation, the device of FIG. 7B houses DNA colonies 759 in a detection regions 765. The surface of the transparent support member 757 is functionalized so that a DNA molecule is selectively attached in a detection region 765. PPi and or Pi molecules are generated when polyphosphate molecules are released from DNA polymerase sequencing reactions (as described herein). The surface of the transparent support member 757 additionally optionally comprises immobilized dye molecules (not shown) that are capable of selectively binding PPi or Pi and changing their absorbance pattern upon selectively binding PPi or Pi. Dye molecules that are capable of selectively recognizing PPi or Pi include for example those reported in Kim, S. K., et al, "Chemiosensors for Pyrophosphate," *Acc. Chem. Res.*, 42, 23-31 (2009). In general, selective dyes for PPi or Pi are, for example, dyes that are conjugated to a chelator moiety that is specific for PPi or Pi. The immobilized selective binding dye molecules change absorbance after PPi or Pi binding so that either less light reaches the sensors 765 or more light reaches the sensors 765.

Additional devices that are useful as sensors for detecting reaction products of nucleic acid synthesis and ligation reactions and performing nucleic acid sequencing according to embodiments of the invention also include FETs (field effect transistors), impedance, capacitance, amperometry and cyclic amperometry/voltammetry devices (electrode-based sensors), and combinations of sensing schemes. Sensing schemes include ones that measure or otherwise provide a response based on the primary reaction product content, such as for example PPi, Pi, and $H^+$. In the alternative, sensing schemes can detect the presence of labels (such as fluorescent or redox labels) and or the products of additional chemical reactions, such as for example, detecting the presence of photons (e.g., FIGS. 7A-B), electron carriers, and or redox centers.

Electronic sensors employing electrodes are capable of measuring the impedance, the resistance, the capacitance, and or the redox potential of the materials that are located on or near the electrode surface. In some instances the current at an electrode is measured as a function of applied DC voltage at the electrode-solution interface. Typically, impedance measurements involve measuring the electrical impedance at the electrode-solution interface under AC steady-state conditions and in the presence of a constant DC bias. Electrode-based sensors typically comprise a first electrode that functions as the working electrode, and a second electrode that functions as the counter electrode. Additionally, optionally a third electrode that functions as a reference electrode is also used. A reaction liquid provides an electrical connection between the working electrode and the counter electrode. The molecule(s) to be analyzed are attached to the working electrode or to another structure that forms part of a working sensor device (such as, for example, the walls of a well surrounding the electrodes or substrate material proximate to the electrodes) so that the molecules to be analyzed are proximate to the electrodes. Optionally, a layer of molecules to be detected (molecules that specifically bind a target molecule of interest, such as pyrophosphate or phosphate binding molecules that are capable of specifically recognizing and binding pyrophosphate or phosphate ions) is located above (attached to) the working electrode. An electronic circuit measures impedance (Z), capacitance (C), and or resistance (R). Typically, the current (I) is detected under varying conditions. Impedance, capacitance, and resistance are calculated based on detected current under a given voltage and frequency. The values calculated depend on the circuit model used. See, for example, Daniels, J. S., Pourmand, N., *Electroanaylsis,* 19, 1239-1257 (2007), Carrara, S., et al., *Sensors & Transducers Journal,* 88, 31-39 (2008), Carrara, S., et al., *Sensors & Transducers Journal,* 76, 969-977 (2007), and Wang, J. Carmon, K. S., Luck, L. A., Suni, I. I., *Electrochemical and Solid-State Letters,* 8, H61-H64 (2005). Optionally the circuit 635 is an integrated circuit. Electronics providing input and output control are optionally housed in the substrate, such as in an integrated circuit chip, or are provided through circuitry that is external the substrate.

Electrodes used in electronic sensing applications are comprised of a conducting material that is selected to be inert under reaction conditions, such as for example, gold or platinum. In further embodiments the electrodes made from metals, combinations of metals, or other conducting materials. For example, an electrode may be made from, platinum, palladium, nickel, copper, iridium, aluminum, titanium, tungsten, gold, rhodium, as well as alloys of metals, conducting forms of carbon, such as glassy carbon, reticulated vitreous carbon, basal plane graphite, edge plane graphite, graphite, indium tin oxide, conducting polymers, metal doped conducting polymers, conducting ceramics, and conducting clays. The electrode surface is optionally modified, such as for example, through the silanation of the surface as a mechanism to facilitate coupling of molecules (analytes) to the surface of the sensor.

Further, for the detection of a redox label or species, the device can be a redox cycling sensor, such as, for example, those described in "Nanogap Chemical and Biochemical Sensors," U.S. patent application Ser. No. 12/655,578, filed Dec. 31, 2009. In general, redox cycling is an electrochemical method in which a molecule that can be reversibly oxidized and or reduced (i.e., a redox active molecule) moves between at least two electrodes that are biased independently, one below a reduction potential and the other one above an oxidation potential for the redox active molecule being detected, shuttling electrons between the independently biased electrodes (i.e., the molecule is oxidized at a first electrode and then diffuses to a second electrode where it is reduced (or vice versa, it is first reduced and then oxidized, depending on the molecule and the potentials at which the electrodes are biased)). In redox cycling, the same molecule contributes a plurality of electrons to the recorded current resulting in the net amplification of the signal. In redox cycling applications, the space between the electrodes is on the nanometer scale. Redox-active molecules diffuse in the cavity between the two electrodes and shuttle multiple electrons between the electrodes, leading to amplification of the measured electrochemical current. Signals from the redox active species are potentially amplified greater than 100 times, depending on factors, such as the stability of the redox species and the diffusion rate of the redox species out of the sensing region. Electronic sensors are reliably fabricated in a CMOS (complementary metal oxide semiconductor) compatible manner allowing dense integration of sensor units (and optionally driving electronics) onto a single platform, such as for example a chip or silicon wafer typically used in integrated circuit manufacturing applications.

During a sequencing reaction involving nucleotide incorporation, charged phosphates, polyphosphates, or phosphate-containing complexes and protons are generated. These compounds can affect the potential or current flow of an electronic sensor surface. When a sensor surface is coated with an affinity agent, such as a PPi or phosphate chelator (see, for example, "Solid Phase Chelators and Electronic Biosensors" U.S. patent application Ser. No. 12/655,459, filed Dec. 30, 2009), the surface potential or charge distribution will be affected due to binding of the charged species on the surface of the sensor. In this case, FET devices are used as sensor. When an affinity agent is not used, transient changes in potential or current can also take place due to difference in diffusion rates of the positively charge protons and the negatively charged phosphate compounds, the transient imbalance of local charge distribution can cause either a potential difference or a current flow difference, that can be sensed by either voltage-based or current-based sensing methods. In this embodiment, the sensor surface is a metal (such as, for example, that of an extended gate FET device). When the metal sensor surface is exposed to an aqueous solution, depending on solution pH and the metal sensor's surface modification(s), the surface is likely to be rich either in positively charged or negatively species. When the sensor surface is rich in negatively charged species, it will attract protons generated in a nucleotide incorporation reaction. When the sensor surface is rich in positively charged species, the surface will attract more negatively charged phosphate compounds. These transient or constant surface interactions can also affect the surface potential and can be detected by voltage-based sensing methods or current-based sensing methods or a combination of methods, such as impedance-based sensing methods. In general, a sensor device has a sensing surface comprising metal with a metal interconnect that is functionally linked to a semiconductor sensing circuit. The sensing circuit is functionally connected to a semiconductor control circuit for sensor address, signal processing, signal input/output and power. A circuit is set of integrated electronic elements designed for desired functions. Different circuits or multiple circuits can be fabricated on the same support substrate such as a silicon wafer.

Figure 8:
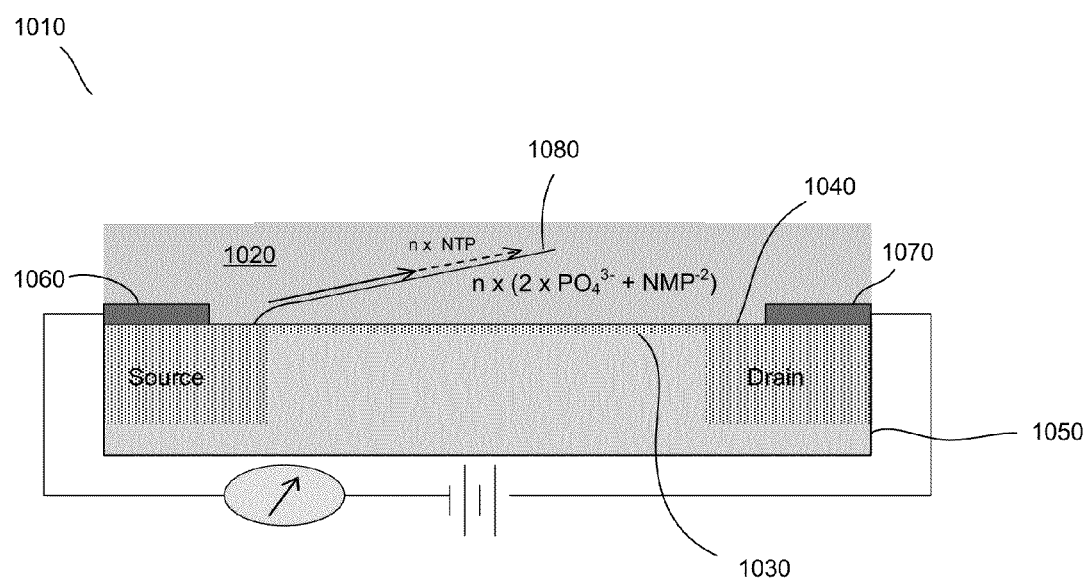
FIG. 8 is a schematic of device employing a field effect transistor that can be used for analyzing a solution-based nucleic acid sequencing reaction.

FIG. 8 shows a FET type sensor that is used for sensing a change in reactant or product concentrations resulting from DNA synthesis reactions, such as, for example, a change in PPi concentration. In sensor device 1010, the amplified chemical signals from nucleic acid synthesis reactions are converted into an electronic signal by an electronic sensing region 1030. For example, the sensor can be a P-type FET, an N-type FET, or a carbon nanotube transistor. See, for example, Janicki, M., Daniel, M., Szermer, M., Napieralski, A., *Microelectronics Journal,* 35, 831-840 (2004) and Rolka, D., Poghossian, A., Schoning, M., *Sensors,* 4, 84-94 (2004). In one embodiment, each sensor has a nano-sized reaction region 1020 (the gate) and a semiconductor transistor (channel) 1030 that are separated by an insulating layer 1040. The insulating layer 1040 is, for example, made from silicon oxide, silicon nitride, aluminum nitride, and or silicon oxynitride. The channel 1030 of the semiconductor transistor is comprised of, for example, a P- or N-type semiconductor, such as for example, silicon or germanium doped with boron, arsenic, phosphorous, or antimony. A solution in the reaction region 1020 forms a gate and the components of the sensor

1010 are typically placed on a substrate 1050. The source electrode 1060 and the drain electrode 1070 are typically comprised of conducting materials, such as for example, gold, copper, silver, platinum, nickel, iron, tungsten, aluminum, or titanium. The substrate 1050 is comprised of, for example, silicon, silica, quartz, germanium, or polysilicon. In further embodiments, the reaction region 1020 has dimensions of less than about 100 nm, less than about 1 µm, or less than about 10 µm. The reaction region can have dimensions in the range of 10 nm to 10 µm. The reaction region 1020 is used as part of the gate of the transistor. DNA 1080 is immobilized through attachment to a sensor surface by standard methods. For example, acrydite-modified DNA fragments can be attached to a surface modified with thiol groups and amine-modified DNA fragments can be attached to epoxy or aldehyde modified surfaces. In operation, variations in the potential between the solution (the gate) in the reaction region 1020 and the insulator 1040 surface modify the charge distribution in the channel 1030. Changes in the solution, such as changes in charge distribution created by the linearly amplified PPi molecules or bound charges associate with the DNA molecules, can be measured by changes in the conductivity or changes in the capacitance across the channel 1030. The sensor 1010 is optionally one of a plurality of sensors that forms an array of sensors.

Alternatively, extended gate FET sensor is used. An extended gate is a metal that is functionally connected to a FET device that is made by, for example, CMOS process. The metal of the extended gate has a surface area that is functionally connected to a region where a biochemical (sequencing) reaction takes place. The metal extended gate can be built in a process similar to the process used to build the interconnects on top of silicon substrate where FET sensors are located. The exposed surface of the extended gate is made of electrochemically stable noble metals, such as, Au, Pt, or Pd.

Arrays of FETs and extended gate FET devices are used to sequence nucleic acids. For example, arrays of sensors comprise from $10^2$ to as many as $10^{10}$ sensors, from $10^4$ to $10^9$, from $10^4$ to $10^8$, from $10^4$ to $10^7$, or from $10^3$ to $10^6$ sensors. The sensors of the array are be monitored individually or as a group. Additionally, an optical fluorescence imager (or a scanner) (not shown) is employed above the array to image fluorescent labels.

In general, a sensor array allows many immobilized DNA colonies to be sequenced simultaneously. DNA density in the sensor regions is controlled, for example, by dilution. Typically, DNA molecules to be immobilized are diluted so that statistically each sensor has one DNA molecule immobilized in the sensing region. Information from sensors showing ambiguous results can be disregarded. DNA colonies are created after the DNA fragment is immobilized. In some embodiments, sequence information is assembled from the sensors having a single DNA colony immobilized. Chemical information, such as for example a change in reaction product concentration, or optical data, from each reaction region is sensed (or measured) independently. Micro and nano-structures on the array are optionally built to minimize diffusion. For example, wells can be built over or around each sensor, or the sensor well array can be placed upside down, well facing down, with the temperature in the down side lower than the chip side, and a low melting point gel (such as low melting point agarose) can be used to make the reaction mixture. Standard silicon and semiconductor processing methods allow a highly integrated sensor array to be made. For example, a 2.5×5 cm² silicon wafer chip can hold as many as 5×10⁹ sensors that are about 0.5×0.5 µm². A reaction region is optionally a cavity, a well, or a depression in the surface of the substrate that is capable of containing a liquid or gel.

In alternate embodiments, the array surface containing many sensors is uniformly modified and the end of different DNA molecules are also uniformly modified so that the DNA molecules can be chemically (through cross-linking, for example) or biochemically (through affinity binding) attached to the surface of the sensor. Density is controlled, for example, through dilution. For a large array containing millions or billions of sensors, the same DNA molecule can be in different sensors. To sequence a human genome, for example, the data typically have to be more than 10× redundant to achieve high accuracy.

Optionally some or all of the electronics for sensing and recording data are integrated circuits that are part of the substrate that house an array of electronic sensors. Electronics providing input and output control are optionally housed in the substrate, such as in an integrated circuit chip, or are provided through circuitry that is external to the substrate. An array of sensing electrodes is optionally equipped with circuitry for individually addressing the electrodes, driving the electrodes at selected voltages, memory for storing voltage current information to be supplied to the electrodes, memory and microprocessors for measuring electrode characteristics, differential amplifiers, current-sensing circuits (including variants of circuits used in CMOS image sensors), and or field effect transistors (direct and floating gate). Alternatively, one or more of these functions can be performed by external instruments and or attached computer system.

The nucleic acid sequencing methods are optionally integrated into a miniaturized device, such as a microfluidic or a nanofluidic device. Additionally, the nucleic acid sequencing methods according to embodiments of the invention are automated though the use of a computer to control the delivery of reagents and monitor the results from electrical or optical measurements, such as current flow in FETs, impedance between electrodes, redox potentials of labels, and or fluorescence detection. Sequence data is assembled from multiple cycles of reactions. Microscale fluidic devices typically have interior features for fluid flow and containment having diameters of 500 µm or less. Nanoscale fluidic devices typically have interior features for fluid flow and containment having diameters of 500 nm or less.

In general, arrays of sensors are formed in a pattern or a regular design or configuration or alternatively are randomly distributed sensors. In some embodiments, a regular pattern of sensors are used the sensors are addressed in an X-Y coordinate plane. The size of the array will depend on the end use of the array. Arrays containing from about two to many millions of different discrete sensors can be made. Very high density, high density, moderate density, low density, or very low density arrays are made. Some ranges for very high-density arrays are from about 100,000,000 to about 1,000,000,000 sensors per array. High-density arrays range from about 1,000,000 to about 100,000,000 sensors. Moderate density arrays range from about 10,000 to about 100,000 sensors. Low-density arrays are generally less than 10,000 cavities. Very low-density arrays are less than 1,000 sensors.

Persons skilled in the relevant art appreciate that modifications and variations are possible throughout the disclosure and combinations and substitutions for various components shown and described. Reference throughout this specification to "one embodiment" or "an embodiment" means that a particular feature, structure, material, or characteristic described in connection with the embodiment is included in at least one embodiment of the invention, but does not necessarily denote that they are present in every embodiment. Furthermore, the particular features, structures, materials, or characteristics may be combined in any suitable manner in one or more embodiments. Various additional structures may be included and or described features may be omitted in other embodiments.

The invention claimed is:

1. A method for analyzing a nucleic acid comprising,
fragmenting a sample of DNA and circularizing the fragments of DNA,
attaching the circularized fragments of DNA to a substrate surface in regions of the substrate surface that are capable of being monitored by sensors wherein each region is capable of being monitored by one sensor and a plurality of regions capable of being monitored by a sensor each comprise one attached circularized fragment of DNA,
forming colonies of DNA from the attached circularized fragments of DNA wherein each of the colonies is a DNA molecule that is comprised of seven to 100 regions wherein the regions have the same sequence of nucleotides,
hybridizing a set of primer molecules to each of the colonies wherein each of the primer molecules in the set of primer molecules has the same sequence of nucleotides,
providing reactants to the DNA colonies comprising a nucleoside polyphosphate, comprising four to six phosphates, an enzyme capable of extending a DNA molecule, and an enzyme capable of deconstructing a DNA molecule under conditions that allow DNA to be extended and deconstructed, wherein the primer molecule is extended by a nucleoside polyphosphate complementary to a base of the attached DNA colony and deconstructed to remove the complementary nucleoside from the primer molecule a plurality of times;
monitoring the sensors to detect increases in reaction products to determine the identity of the nucleoside that is complementary to a base of the attached DNA colony;
terminating the primer molecule with an exonuclease resistant nucleoside polyphosphate comprising three to six phosphates having a base that has been identified as complementary to a base of the attached DNA strand;
repeating the elements of providing reactants to the DNA colonies and monitoring the sensors at least one time; and
determining sequence information for the sample of DNA to be sequenced based on increases in reaction products detected by the sensors.

2. The method of claim 1 wherein the sensors are field effect transistors or extended gate field effect transistors.

3. The method of claim 1 wherein the sensors are capacitance sensitive sensors comprised of metal electrodes.

4. The method of claim 1 wherein the sensors are impedance sensitive sensors comprised of metal electrodes.

5. The method of claim 1 wherein the exonuclease resistant nucleoside polyphosphate is also 3' blocking and the method additionally comprises deblocking the attached exonuclease resistant 3' blocking nucleoside.

6. The method of claim 1 wherein the regions capable of being monitored by a sensor additionally comprise molecules that are capable of binding phosphate or pyrophosphate, that are capable of emitting light before the binding of phosphate or pyrophosphate or emitting light after the binding of phosphate or pyrophosphate, and that are capable of changing light emission properties after the binding of phosphate or pyrophosphate.

7. The method of claim 6 wherein the sensors charge-coupled devices, single photon avalanche diodes, or complementary metal oxide sensors.

8. The method of claim 1 wherein the substrate is comprised of about 10,000 to about 1,000,000,000 regions that are capable of being monitored by sensors.

9. The method of claim 1 wherein the array is comprised of about 1,000 to about 1,000,000 regions that are capable of being monitored by sensors.

10. The method of claim 1 wherein the primer molecules are exonuclease resistant.

11. A method for analyzing a nucleic acid comprising,
fragmenting a sample of DNA and circularizing the fragments of DNA,
attaching the circularized fragments of DNA to a substrate surface in regions of the substrate surface that are capable of being monitored by sensors capable of detecting fluorescence wherein each region is capable of being monitored by a sensor and a plurality of regions capable of being monitored by a sensor each comprise one attached circularized fragment of DNA,
forming colonies of DNA from the attached circularized fragments of DNA wherein each of the colonies is a DNA molecule that is comprised of seven to 100 regions wherein the regions each have the same sequence of nucleotides,
hybridizing a set of primer molecules to each of the colonies wherein each of the primer molecules in the set of primer molecules has the same sequence of nucleotides,
determining the identity of a nucleotide of the DNA to be sequenced through the detection of a fluorescently labeled complementary nucleotide incorporated into the primer molecules;
removing any nucleotides incorporated into the primer molecules during the determination of the identity of the nucleotide of the DNA to be sequenced;
ligating an oligonucleotide from a set of oligonucleotides comprised of a first nucleotide complementary to the known nucleotide, a second nucleotide adjacent to the first nucleotide and complementary to a nucleotide adjacent to the known nucleotide of the DNA colony, a third nucleotide adjacent to the second nucleotide and complementary to a nucleotide of the DNA colony, wherein the third nucleotide is exonuclease resistant, and wherein within the set of oligonucleotides either the second or the third nucleotide is the same in each oligonucleotide in the set, 4 to 7 universal nucleotides, and a fluorescent label attached to a universal nucleotide, wherein the fluorescent label is indicative of the identity of the either the second or the third nucleotide which is not the same in each oligonucleotide in the set, to the primer molecules;
detecting the fluorescent label from the ligated oligonucleotide to determine the identity of the second or third complementary nucleotide;
digesting universal nucleotides from the primer strand;
repeating the elements of ligating an oligonucleotide, and detecting the fluorescent label; and
assembling sequence information for at least six nucleotides of the DNA colony.

12. The method of claim 11 wherein the sensors are charge-coupled devices, single photon avalanche diodes, or complementary metal oxide sensors.

13. The method of claim 11 wherein the substrate is comprised of about 10,000 to about 1,000,000,000 regions that are capable of being monitored by sensors.

14. The method of claim 11 wherein the array is comprised of about 1,000 to about 1,000,000 regions that are capable of being monitored by sensors.

15. The method of claim 11 wherein the primer molecules are exonuclease resistant.

16. A method for analyzing a nucleic acid comprising,
fragmenting a sample of DNA and circularizing the fragments of DNA,
attaching the circularized fragments of DNA to a substrate surface in regions of the substrate surface that are capable of being monitored by fluorescence detecting sensors wherein each region is capable of being monitored by a sensor and a plurality of regions capable of being monitored by a sensor each comprise one attached circularized fragment of DNA,
forming colonies of DNA from the attached circularized fragments of DNA wherein each of the colonies is a DNA molecule that is comprised of seven to 100 regions wherein the regions each have the same sequence of nucleotides,
hybridizing a set of primer molecules to each of the colonies wherein each of the primer molecules in the set of primer molecules has the same sequence of nucleotides,
ligating an oligonucleotide from a set of oligonucleotides comprising a first, second, and third nucleotide complementary to a first, second, and third nucleotide of the DNA colony, wherein the second nucleotide is exonuclease resistant, and wherein within the set of oligonucleotides either the second or the third nucleotide is the same in each oligonucleotide in the set, 4 to 7 universal nucleotides, and a fluorescent label attached to a universal nucleotide, wherein the fluorescent label is indicative of the identity of the either the second or the third nucleotide which is not the same in each oligonucleotide in the set, to the primer molecules;
detecting the fluorescent label from the ligated oligonucleotide to determine the identity of a second or third complementary nucleotide;
digesting nucleotides from the primer strand until the exonuclease resistant nucleotide is reached;
repeating the elements of ligating an oligonucleotide, and detecting the fluorescent label; and
assembling sequence information for at least four nucleotides of the DNA colony.

17. The method of claim 16 wherein the sensors are charge-coupled devices, single photon avalanche diodes, or complementary metal oxide sensors.

18. The method of claim 16 wherein the substrate is comprised of about 10,000 to about 1,000,000,000 regions that are capable of being monitored by sensors.

19. The method of claim 16 wherein the array is comprised of about 1,000 to about 1,000,000 regions that are capable of being monitored by sensors.

20. A method for analyzing a nucleic acid comprising,
fragmenting a sample of DNA and circularizing the fragments of DNA,
attaching the circularized fragments of DNA to a substrate surface in regions of the substrate surface that are capable of being monitored by fluorescence detecting sensors wherein each region is capable of being monitored by a sensor and a plurality of regions capable of being monitored by a sensor each comprise one attached circularized fragment of DNA,
forming colonies of DNA from the attached circularized fragments of DNA wherein each of the colonies is a DNA molecule that is comprised of seven to 100 regions wherein the regions each have the same sequence of nucleotides,
hybridizing a set of primer molecules to each of the colonies wherein each of the primer molecules in the set of primer molecules has the same sequence of nucleotides,
ligating an oligonucleotide from a set of oligonucleotides comprising a first, second, and third nucleotide complementary to a first, second, and third nucleotide of the DNA colony, wherein the third nucleotide is ribonuclease sensitive, and wherein within the set of oligonucleotides either the second or the third nucleotide is the same in each oligonucleotide in the set, 4 to 7 universal nucleotides, and a fluorescent label attached to a universal nucleotide, wherein the fluorescent label is indicative of the identity of the either the second or the third nucleotide which is not the same in each oligonucleotide in the set, to the primer molecules;
detecting the fluorescent label from the ligated oligonucleotide to determine the identity of a second or third complementary nucleotide;
cleaving the ligated oligonucleotide at the ribonuclease sensitive nucleotide to remove the ribonuclease sensitive nucleotide and universal nucleotides;
repeating the elements of ligating an oligonucleotide, and detecting the fluorescent label; and
assembling sequence information for at least four nucleotides of the DNA colony.

21. The method of claim 20 wherein the sensors are charge-coupled devices, single photon avalanche diodes, or complementary metal oxide sensors.

* * * * *